(12) United States Patent  (10) Patent No.: US 8,349,609 B2
Dealy et al.  (45) Date of Patent: Jan. 8, 2013

(54) DIFFERENTIATION OF HUMAN EMBRYONIC AND INDUCED PLURIPOTENT STEM CELLS

(75) Inventors: Caroline Dealy, Farmington, CT (US); Robert Kosher, Farmington, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 12/954,088

(22) Filed: Nov. 24, 2010

(65) Prior Publication Data

US 2011/0229440 A1  Sep. 22, 2011

Related U.S. Application Data

(60) Provisional application No. 61/264,170, filed on Nov. 24, 2009.

(51) Int. Cl.
*C12N 5/00* (2006.01)
*C12N 5/02* (2006.01)
*C12N 5/10* (2006.01)
*C12N 5/071* (2010.01)

(52) U.S. Cl. .................. 435/377; 435/363; 435/366

(58) Field of Classification Search .................. None
See application file for complete search history.

(56) References Cited

U.S. PATENT DOCUMENTS

| 2002/0061514 | A1 | 5/2002 | Underhill et al. |
| 2003/0109038 | A1 | 6/2003 | Thies et al. |
| 2007/0042491 | A1 | 2/2007 | Karp et al. |
| 2009/0029462 | A1 | 1/2009 | Beardsley et al. |
| 2009/0098177 | A1 | 4/2009 | Werkmeister et al. |
| 2009/0136559 | A1 | 5/2009 | Athanasiou et al. |

FOREIGN PATENT DOCUMENTS

| KR | 1020070025607 | 8/2007 |
| WO | 2006131722 | 12/2006 |

OTHER PUBLICATIONS

Embryoid Body Formation [online], 2006 [retrieved Mar. 30, 2012]. Retrieved from the Internet:< URL: http://www.atcc.org/Portals/1/Embryoid_Body_Formation.pdf>, pp. 1-2.*
Schuldiner et al., 2000, PNAS, USA, 97: 11307-11312.*
Gay and Kosher (1984) J Exp Zool, 232: 317-326.
Kosher, et al. (1986) Dev Biol, 118: 112-117.
Kosher, et al. (1986) J Cell Biol, 102: 1151-1156.
Kulyk, et al. (1991) Matrix, 11 :282-288.
Waese and Stanford (2010) Stem Cell Res Sep. 6.
Nakagawa, et al. (2009) Arthritis Rheum 60: 3686-3692.
An, et al. (2010) Ann Biomed Eng 38: 1647-1654.
Moore, et al. (2010) J Clin Periodontol 37: 288-298.
Zazlav, et al. (2009) Am J Sports Med, 37:42-55.
Jubel, et al. (2008) Am J Sports Med 36: 1555-1564.
Erggelet, et al. (2003) Arthroscopy, 19:108-110.
Kon, et al. (2009) Am J Sports Med 37: 156s-166s.
Brittberg, (2010) Am J Sports Med, 38: 1259-1271.
Gobbi, et al. (2006) Am J Sports Med 34: 1763-177.
Giannini et al. (2008) Am J Sports Med 36:873-880.
Nixon (2002) Clinical Tech Equine Practice 1: 257-269.
Funayama, et al. (2008) J Orthop Surg 13: 225-232.
Hoemann, et al. (2005) Osteoarthritis Cast 13: 318-329.
Emans, et al. (2010) PNAS 107:3418-3423.
Centeno, et al. (2008) Pain Physician 11: 343-353.
Horie, et al. (2009) Stem Cells 27:878-887.
Lee, et al. (2007) Stem Cells 25:2964-2971.
Murphy, et al. (2003) Arthritis Rheum 48:3464-3474.
Petrella and Petrella (2006) J Rheumatol 33: 951-956.
Brander and Stadler (2009) Phys Sports Med 37: 38-48.
Hunter, et al. (2010) BMC Musculoskelet Disord 11:232.
Hayashi, et al. (2010) J Orthop Res 28: 1502-1506.
Centano, et al. (2008) Med Hypotheses 71 :900-908.
Goldstein (2006) J Am Acad Orthop Surg 14: S152-156.
Sundelacruz and Kaplan (2009) Sem Cell Dev Biol, 20: 646-655.
Kronenberg (2003) Nature, 423: 332-336.
Kallai, et al. (2010) J Biomech 43: 2315-2320.
Scotti, et al. (2009) PNAS 107: 7251-7256.
Muller, et al. (1999) Stem Cell Dev Biol, 10: 405-413.
Gurtner, et al. (2007) Ann Rev Med 58:299-312.
Muneoka, et al. (2008) Sci Am 298:56-63.
Han, et al. (2008) Dev Biol, 315: 125-135.
Amabile and Meissner (2009) Trends Molec Med 15: 59-68.
Laustriat, et al. (2010) Biochem Soc Trans 38: 1051-1057.
Krakow and Rimoin (2010) Genet Med 12: 327-341.
Pogue, et al. (2004) Matrix Biol, 23: 299-307.
Wong and Chiu (2010) Biotechnol Adv Jul. 24.
Chu, et al. (2010) Tissue Eng Part B 16: 105-115.
Kubo, et al. (2009) Arthritis Rheum 60: 155-165.
Kameltura, et al. (2005) Osteoarthritis Cart 13: 632-641.
Glasson, et al. (2007) Osteoarthritis Cart 15: 1061-1069.
Welch, et al. (2009) Arthritis Res Ther, 11:R14.
Ahern, et al. (2009) Osteoarthritis Cast 17: 705-713.
Dausse, et al. (2003) Osteoarthritis Cast 11: 16-28.
Eltawil, et al. (2009) Osteoarthritis Cart 17:695-704.
Thomson, et al. (1998) Science, 282: 1145-1147.
Toh, et al. (2007) Stem Cells, 25:950-960.
Akiyama, et al. (2002) Genes and Development 16:2813-2828.
Lefebvre and Smits (2005) Birth Defects Res C Embryo Today, 75:200-212.
Herrmann (1995) Seminars in Developmental Biology, 6:385-394.
Hoffmann, et al. (2002) J Cell Sci, 115:769-781.
Liu, et al. (2003) Development, 130: 1327-1337.
Han and Lefebvre (2008) Molecular and Cellular Biology, 28:4999-5013.
Nah and Upholt, (1991) J Biol Chem, 266:23446-23452.
Sakai, et al. (2001) Matrix Biol, 19:761-767.
Lengner (2010) Ann NY Acad Sci 1192: 38-44.
Piersma (2004) Toxicol Lett 149:147-153.
Ponce (2001) Curr Protoc Toxicol 13: 13.3.

(Continued)

*Primary Examiner* — Joanne Hama

(74) *Attorney, Agent, or Firm* — McDonnell Boehnen Hulbert & Berghoff LLP

(57) ABSTRACT

The invention relates to culture systems, methods, and conditions that allow pluripotent undifferentiated hESCs or iPSCs to progressively and uniformly differentiate into cells of the chondrogenic lineage.

28 Claims, 12 Drawing Sheets

OTHER PUBLICATIONS

James, et al. (2005) Mol Biol Cell 16:5316-5333.
Hansen et al. (2001) Free Radic Biol Med 31: 1582-1592.
Woods, et al. (2007) Endocrinol 148:5030-5041.
Sakharov, et al. (2008) Bull Exp Biol Med, 146:124-8.
Elvenes, et al (2009) J Orthop Sci, 14:410-7.
Hayes, et al (2008) J Histochem Cytochem, 56:125-38.
Martin, et al. (2005) Biotechnol Prog, 21:168-77.
ISR from PCT/US10/58024, mailed Feb. 11, 2011.
Ginis I, et al. (2004). Dev Biol 269: 360-380.
Poon E, et al. (2006) J Cell Sci. 119: 759-768.
Chin, et al. (2009) Cell Stem Cell 5: 111-123.
Doi, et al. (2009) Nat. Genet. 41: 1350-1353.
Hu, et al. (2010) Proc. Natl. Acad. Sci. USA 107: 4335-4340.
Yu L, et al. (2010) Development 137: 551-559.
Rinkevich, et al. (2011) Nature 476: 409-414.
Pearl, et al. (2008) BMC Dev Biol. 8:66.
Yamashita, et al. (2009) Cell Death Differ, 16(2): 278-286.
Matthews, et al. (2003) J. Bone Joint Surg.-Brit vol. 88-B(Supp_III):375 abstract.
Schibler, et al. (2009) PLoS One, article e7633, 4(10):1-11.
Toh, et al (2007) Stem Cells, 25(4):950-960.
Hwang, et al. (2008) Stem Cells Dev., 17(5):971-978.
Magne, et al (2005) Trends in Molecular Medicine, 11:519-526.
Song, et al. (2004) Cytotherapy, 6:596-601.
Elisseeff, et al. (2005) Orthod Craniofac Res, 8: 150-161.
Harkness et al. (2009) Stem Cell Rev 5:353-368.
Heng, et al. (2004) Stem Cells, 22:1152-1167.
Hoben, et al. (2009) Stem Cells Dev 18:283-292.
Hwang, et al. (2006) Stem Cells, 24:284-291.
Hwang, et al. (2008) PLoS One, 3:1-10.
Hwang, et al. (2006) Tissue Eng, 12:2695-2706.
Jukes, et al. (2008) Tissue Engineering Part A, 14:135-147.
Kawaguchi, et al. (2005) Bone, 36:758-769.
Koay, et al. (2007) Stem Cells 25:2183-2190.
Koay and Athanasiou (2009) Tissue Eng Part A 15:2249-2257.
Kramer, et al. (2000) Mechanisms of Development, 92: 193-205.
Kramer, et al. (2005) Cell Biology International, 29: 139-146.
Kramer, et al. (2005) Anat Embryol, 210: 175-185.
Ofek, et al. (2009) J Biomech Eng 131: 061011.
Sui, et al. (2003) Differentiation, 71:578-585.
Toh, et al. (2009) J Cell Mol Med 13B: 3570-3590.
Vats, et al. (2006) Tissue Eng 12:1687-1697.
Nieden, et al. (2005) BMC Dev Biol, 5:5-15.
Yamashita, et al. (2010) PLoS One, 5:e10998.
Macias, et al. (1997) Development, 124 : 1109-1117.
Watanabe, et al., (2007) Nature Biotechnology, 25 : 681-686.
Li, et al. (2009) Human Reproduction 24: 580-589.
Lee, et al. (2010) Tissue Eng A 16:705-717.
Brown, et al. (2008) Cells Tiss Org, 189:256-260.
Mahmood, et al. (2010) J Bone Min Res 25: 1216-1233.
Cohen, et al. (2010) Tissue Eng A 16: 3119-3139.
Varghese, et al. (2010) Stem Cells 28: 765-774.
Barberi T et nl., 2005 PLoS Med 2 e161.
Bigdeli N et al. (2009) Stem Cells 27:1812-1821.
Lian, et al. (2007) Stem Cells 25:425-436.
Kopher, et al. (2010) Bone 47:718-728.
Stavropoulos, et al. (2009) Curr Prot Stem Cell Biol 9:1F.8.1-1F.8.10.
Barberi, et al. (2007) Nature Med 13: 642-651.
Asponmeaklong, et al. (2009) Stem Cells Dev 18:955-968.
Boyd, et al. (2009) Tissue Eng A 15:1897-1908.
Medvedev, et al. (2010) Stem Cells Dev.
Lian, et al. (2010) Circulation 121 : 1113-1123.
Fisher, et al., (2006) Matrix Biology, "Heparan sulfate proteoglycans including syndecan-3 modulate BMP activity during limb cartilage differentiation" vol. 25, pp. 27-39.

* cited by examiner

Table 1. Percentage of cells surrounded by Alcian blue positive matrix
BMP2-treated                88.0%
BMP2 + TGFβ1                97.3%

A.

B.

DIFFERENTIATION OF HUMAN EMBRYONIC AND INDUCED PLURIPOTENT STEM CELLS

RELATED APPLICATION INFORMATION

This application claims priority to U.S. Provisional Patent Application Ser. No. 61/264,170, filed on Nov. 24, 2009.

FIELD OF THE INVENTION

The invention generally relates to methods for directing the differentiation of human embryonic and induced pluripotent stem cells into the cartilage lineage.

BACKGROUND OF THE INVENTION

Degenerative diseases of cartilage, e.g., osteoarthritis, are among the most prevalent and debilitating chronic health problems in the United States. Treatment of degenerative cartilage diseases is a particular clinical challenge because of the limited capacity of the tissue for self-repair. Because of their ability to differentiate into multiple cell types and their unlimited capacity for self-renewal, human embryonic stem cells (hESCs) are a potentially powerful tool for the repair of cartilage defects. Fulfilling the potential of hESCs for repair of diseased and damaged cartilage requires developing methods for directing their differentiation into the chondrogenic lineage.

Although several culture systems have been developed in which ESC-derived cells differentiate to various degrees into chondrocytes, in these systems chondrogenic differentiation is not uniform, and chondrocytes represent only a subpopulation of the cells that differentiate, complicating utilization of the cell population for cartilage repair. Prior to the invention described below, most of the chondrogenic differentiation protocols utilized cells of embryoid bodies (EBs) derived from ESCs. A drawback of such earlier methods is that the cellular heterogeneity of EB-derived cells hinders the ability to obtain homogeneous populations of chondrogenic cells that can be used for cartilage repair.

SUMMARY OF THE INVENTION

The invention solves many of the problem associated with such earlier methods and is based, in part, on culture systems and conditions that promote the rapid, direct, progressive, and substantially uniform differentiation of stem cells such as undifferentiated pluripotent human embryonic stem cells (hESCs) or induced pluripotent stem cells (iPSCs or iPS cells) into the chondrogenic lineage without prior EB formation. Stem cells obtained from cord blood or amniotic fluid are also used in the methods. The substantially pure chondrogenic cells at defined stages of differentiation that are produced using the methods provide a solution to the problems and drawbacks of cell heterogeneity (with respect to tissue type as well as stage of differentiation) associated with prior methods. The cell populations described herein are substantially free of non-chondrogenic cells, e.g., the populations comprise at least 85%, 95-98%, and up to 99 or 100% chondrogenic cells. The invention also provides high density culture conditions and additional procedures which promote the progression of the differentiation of ESCs into the chondrogenic lineage and which contribute to the uniformity of chondrogenic differentiation achieved.

Embryoid bodies are aggregates of cells derived from ESCs or from iPSCs. These aggregates or EBs are apparent upon visual inspection of the cultures. Upon aggregation (formation of EBs), differentiation is initiated. EBs differentiate into multiple cell types derived from all 3 germ layers of the embryo that give rise to all of the cell types present in an adult organism. Prior to the invention, a drawback of earlier methods of producing populations of chondrogenic precursor cells from hESC was contamination with non-chondrogenic cells, those non-chondrogenic cells having been generated from EB differentiation into lineages other than the desired target lineage (chondrogenic lineage). Since the methods described herein avoid EB formation, the resulting chondrogenic precursor cells are substantially free from contaminating cells of other lineages. The methods solve the problem of EBs in the culture differentiating into non-chondrogenic tissue/cells. Since earlier methods required removal of contaminating undesirable cells, the process described herein is more efficient, faster, and more cost-effective than previous methods.

A method for direct differentiation of human embryonic stem cells (hESCs) into chondrogenic cells is carried out by providing a population of hESCs on a substrate, said population being substantially free of EBs; detaching the hESCs from said substrate and dissociating said hESCs; establishing a high-density micromass culture of the hESCs; and contacting the population with a bone morphogenetic protein; wherein the hESCs directly differentiate into a substantially uniform population of chondrogenic cells. Similarly, a method for direct differentiation of induced pluripotent stem cells (iPSCs) into chondrogenic cells is carried out by providing a population of iPSCs on a substrate, said population being substantially free of EBs; detaching the iPSCs from the substrate and dissociating the iPSCs; establishing a high-density culture of the iPSCs; and contacting the iPSCs with a bone morphogenetic protein thereby directing the differentiation of iPSCs into the chondrogenic lineage. The iPSCs directly differentiate into a substantially uniform population of chondrogenic cells.

In one aspect, the culture systems and conditions described herein promote substantially uniform cartilage differentiation within less than about 1 or 2 weeks, e.g., about 2 days to about 3 days; about 3 days to about 4 days; about 5 days to about 6 days; about 6 days to about 7 days; about 7 days to about 8 days; about 8 days to about 9 days; about 9 days to about 10 days; about 10 days to about 11 days; about 11 days to about 12 days; about 12 days to about 13 days, or about 13 days to about 14 days. In another aspect, the culture systems and conditions of the invention promote quite uniform differentiation such that at least about 50-100% of undifferentiated pluripotent human embryonic stem cells differentiate into the chondrogenic lineage, e.g., at least about 50-60%; at least about 60-70%; at least about 70-80%; at least about 80-90%; or at least about 90-100% of undifferentiated pluripotent human embryonic stem cells differentiate into the chondrogenic lineage. Preferably, the population comprises 95% chondrogenic cells; more preferably, the population comprises 98% chondrogenic cells.

Stage of differentiation is described temporally or by expression of a panel of genetic markers. Timing (days) reflects the amount of time after the establishment of a high density culture of hESCs or iPSCs. Time zero is the point at which the cell concentration or density is adjusted to at least $1 \times 10^5$ cells per 10 "2 day" cells are cells that have been cultured for 2 days after the establishment of a high density colony. A high density culture comprises cells at a concentration of at least $1 \times 10^5$ per 10 µl. For example, 2-3 day cells are characterized as just entering the cartilage lineage (i.e., chondroprogenitors), day 4 cells are in an early phase of chondrogenic differentiation (i.e., early chondrocytes), and 7-14 day cells have uniformly undergone overt differentiation into chondrocytes but have not undergone hypertrophic maturation (i.e., the cells are characterized as fully differentiated chondrocytes) (FIG. 14).

The invention describes the characterization of hESC-derived progenitor cells in different phases of the chondrogenic lineage, ranging from cells just entering into the chondrogenic lineage to overtly differentiated chondrocytes. hESC-derived progenitor cells in different phases of chondrogenic lineage are analyzed for their ability to repair cartilage using cell based tissue engineering therapies.

The conditions that promote the chondrogenic differentiation of hESCs also promote the uniform cartilage differentiation of induced pluripotent stem cells (iPSCs). The invention also provides methods of direct chondrogenic differentiation of iPSCs derived from patients. For example, iPSC-derived chondrogenic precursor cells (autologous cells) are used for patient-specific therapeutic approaches. In another example, the methods are used to produce cells and cell lines to be used as a research tool to elucidate underlying mechanisms of genetic disorders of cartilage, such as chondrodysplasias, in order to study mechanisms of disease as well as to using the cells to screen for therapeutic agents.

As discussed above, conditions that promote the chondrogenic differentiation of hESCs also promote the uniform cartilage differentiation of induced pluripotent stem cells (iPSCs), i.e., somatic cells that have been reprogrammed to a pluripotent state. Reliable direct and uniform differentiation of iPSCs into the chondrogenic lineage permits patient-specific autologous cell therapy. Thus, iPSCs-derived chondrogenic progenitor cells, as well as hESC-derived precursors, are used to repair cartilage defects.

The culture systems and conditions of the invention avoid the cellular heterogeneity that complicates the use of cells derived from embryoid bodies (EBs) for cell-based cartilage repair therapies. Since the methods promote direct and uniform differentiation and circumvent the EB stage, they reliably yield cell populations at a defined stage of differentiation, i.e., early stage versus late stage. Gene expression profiling enables the identification of hESC-derived progenitor cells in different stages of the chondrogenic lineage, ranging from cells just entering into the chondrogenic lineage to overtly differentiated chondrocytes. In addition to continuing to differentiate, cells in earlier phases of the chondrogenic lineage (e.g., bearing early cartilage markers such as Sox9) respond to local microenvironmental signals in situ after they are transplanted into a recipient and are thus desirable for participation in cartilage repair compared to cells at late stages of the lineage. Cells in late stages of the chondrogenic lineage (e.g., bearing markers indicative of more overtly differentiated cells cartilage markers such as aggrecan) are suitable for cartilage repair/restoration procedures. Thus, unlike earlier methods that yielded a heterogeneous population of cells at various stages of differentiation and different lineages, the present methods provide a source of staged cells and permit fine tailoring of therapies based on the stage of differentiation best suited to the pathological condition to be treated.

The invention also provides conditions and additional procedures which enhance the progression of the differentiation of hESCs and iPSCs into the chondrogenic lineage and which contribute to the uniformity of chondrogenic differentiation achieved. These modifications include: (1) maintenance of the dissociated hESC in high density culture (absence of EBs); (2) supplementation of the cultures with growth factors especially BMP-2 and TGFβ-1; (3) culturing hESCs and iPSCs on or within polymeric or gelatinous substrates or scaffolds rather than on a feeder layer of mouse embryonic fibroblasts; (4) using Accutase, TrypLE Select or other enzymes rather than trypsin for dissociating the hESCs prior to preparing micromass cultures; and, (5) application of a Rho-associated kinase (ROCK) inhibitor, which diminishes dissociation-induced apoptosis, during the establishment of micromass cultures. Suitable polymeric or gelatinous substrate or scaffold materials include basement membrane substrates (e.g. Matrigel, Chondrogide); collagens or gelatins; hydrogels or sponges containing hyaluronan (e.g. Hyaff1 1 or HyStemC) or chitosan; or PEG (poly ethylene glycol) or PLGA (polylacticacidglyolytic acid) scaffolds; or any substrate containing extracellular matrix components.

Specifically, the invention provides methods for directing the differentiation of human embryonic stem cells (hESCs) into the chondrogenic lineage by culturing hESCs in serum-free medium on a substrate; detaching the hESCs from the substrate and dissociating the hESCs; culturing the hESCs as a high-density culture (micromass or pellet) in serum-free medium; and administering bone morphogenetic protein-2 (BMP2; NG_023233 (GI:300068920)), incorporated herein by reference) to the micromass culture medium. The hESCs are substantially free of EBs; preferably the hESCs are completely free of EBs. The BMP2 is administered 12, 24, 48, 72, or 96 hours after initiation of the hESC high-density micromass culture. Preferably, the growth factor(s) are added 48 hours after the establishment of high density cell cultures. Alternatively, BMP-2 and transforming growth factor-beta (TGFβ; NM_000660 (GI:260655621)), incorporated herein by reference) are added together. The concentration of BMP2 is in the range of 25-200 ng/ml, and the concentration of TFGβ1 is in the range of 2.5-20 ng/ml. The ratio of BMP to TGF is approximately 5:1 to 20:1, with a preferred ratio of about 10:1.

The hESCs are contacted with a dissociating agent such as trypsin, TrypLE Select, or Accutase prior to culturing the hESCs as a high-density micromass culture. Optionally, the substrate for hESC culture is a feeder layer comprising mouse embryonic fibroblasts (MEF). Alternatively, the substrate for hESC culture is a gelatinous composition such as artificial basement membrane material (e.g., Matrigel) or other suitable substrate or scaffold. In one aspect, the method further comprises administering transforming growth factor beta-1 (TGFβ1) to the micromass culture medium. Optionally, the method further comprises the administration of a Rho-associated kinase (ROCK) inhibitor.

In one aspect, the hESCs differentiate into cells of the chondrogenic lineage within about 14 days, e.g., within about 10 days; within about 7 days; within about 4 days or within about 3 days. The methods described herein direct the differentiation of cells such that at least about 85% of the hESCs differentiate into cells of the chondrogenic lineage; e.g., at least about 90%; at least about 95%; at least about 98%; at least about 99% or about 100%. The differentiation is preferably carried out in the absence of bovine articular chondrocytes, e.g., differentiated bovine articular chondrocytes. The process is also carried out in the absence of conditioned media from cells, or a cell line such as a hepatocarcinoma cell line.

The invention also provides methods for directing the differentiation of induced pluripotent stem cells (iPSCs) into the chondrogenic lineage by culturing iPSCs in serum-free medium on a substrate; detaching the iPSCs from the substrate and dissociating the iPSCs; culturing the iPSCs as a high-density micromass culture in serum-free medium; and administering bone morphogenetic protein-2 (BMP2) to the micromass culture. The iPSCs are substantially free of EBs;

preferably the iPSCs are completely free of EBs. In one aspect, the iPSCs are derived from a patient with a cartilage disorder. In one aspect, the cartilage disorder is a chondrodysplasia.

The methods described above yield chondrogenic cells, which are characterized by a defined stage of differentiation and by being free of EB-derived cells, e.g., those of non-chondrogenic lineage. For example, the population of chondrogenic cells is substantially free of non-chondrogenic cells, the population having been differentiated from ESCs or iPSCs as described above. In another example, the cell population is synchronized or staged. A uniformly differentiated population of chondrogenic cells contains at least 85% (or 98%, 99%, or 100%) of cells, which are characterized as being at a single defined stage of differentiation. For some clinical applications, the stage of differentiation is relatively early, e.g., the population is substantially free of fully differentiated chondrocytes. For example, the stage is selected from the group consisting of day 3 chondrogenic cells or day 4 chondrogenic cells. Utilization of cells in early phases of the lineage are more responsive to local environmental signals that promote articular cartilage repair after implantation. Thus, a method of repairing or restoring cartilage is carried out by contacting damaged or diseased cartilage with any of the cell populations described above. Similarly, a method of preventing or treating arthritis is carried out by administering to an articulating joint or joint space of an individual (human or other animal, e.g., dog, cat, horse) any of the described chondrogenic cell populations.

The invention includes methods of treating cartilage disorders or defects such as those arising from injury or degeneration. Disorders to be treated include traumatic injuries to articulating joints (e.g., knees including anterior cruciate ligament (ACL) or other ligament tears or ruptures, meniscus tears or fractures), elbows, shoulders (e.g., rotator cuff injury), jaw (temporomandibular joint or TMJ disease) or fingers, and other cartilage or skeletal injuries as well as chronic conditions such as arthritis that develop with age including osteoarthritis (OA), or with inflammation including rheumatoid arthritis (RA), or as a consequence of a traumatic injury, and affecting any of the articulating joints. The cells are useful for prevention of articular cartilage damage due to injury or chronic disease. The cells are also useful for repair of fibrocartilage, ligament or meniscus injury or degeneration. A method of therapy includes the steps of administering the cells produced by the methods herein to a patient with a cartilage disorder, e.g., cartilage injury or arthritis such as osteoarthritis. Therapy also includes introduction of the cells produced by this method to delay or prevent the onset of chronic articular cartilage degeneration due to injury or disease. Methods of repairing cartilage defects with chondrogenic cells produced by the methods involved administering the cells to the articulating joint or other target location by implantation, injection, or infusion. For example, the cells are administered arthroscopically. In some cases, the cells are administered or implanted before, after or during a surgical or arthroscopic procedure to repair an associated defect or condition, e.g., cells are administered to a joint space in conjunction with an ACL repair procedure, meniscus repair, rotator cuff repair, or other procedure. The cells are also useful in methods of regenerating fingers or limbs lost to traumatic injury due to accident or military conflict, or congenital defect.

A significant advantage of the methods is that they permit isolation of substantially pure populations of cells at defined stages of differentiation, e.g., at a stage where cells are just beginning to differentiate (e.g., day 2 cells, day 3 cells, or day 4 cells) or fully differentiated chondrocytes (e.g., day 7-14 cells). Fully differentiated chondrocytes are useful for numerous cartilage repair and restoration therapies. Cells at earlier stages of differentiation are used for the same purpose or for other purposes with the added advantage that they colonize and undergo further differentiation as well as respond to local environmental signals in situ.

The cells produced using the methods described above are also useful to determine the genetic basis of disease and to screen for therapeutic agents to be used to treat or reduce the severity of cartilage disorders. For example, a method of identifying a gene involved in the development of a cartilage disorder is carried out by providing a substantially uniform population of cells at a known stage of differentiation (e.g., day 2-3 cells, day 4 cells, of fully differentiated cells) and detecting an increase or decrease in gene expression compared to normal control cells. An increase or decrease in gene expression indicates that the differentially-expressed gene is involved in the development of the cartilage disorder. For example, the cells are iPSCs obtained from a patient who has been diagnosed with chondrodysplasia or achondroplasia.

An exemplary screening method to identify a therapeutic agent (e.g., a cartilage promoting agent) to treat or reduce the severity of a cartilage disorder is carried out by providing a substantially uniform population of cells at a known stage of differentiation (e.g., day 2-3 cells, day 4 cells, of fully differentiated cells) and contacting the population with a candidate compound and detecting chondrogenesis. An increase in chondrogenesis in the presence of the said compound compared to in the absence of the compound indicates that the compound promotes the formation of cartilage. A decrease in chondrogenesis indicates that the compound inhibits the formation of cartilage.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 9A shows an Alcian blue and Nuclear Fast Red stained sagittal section through day 14 hESC micromass cultures treated with BMP2. Cells surrounded by an Alcian blue stainable extracellular matrix are present throughout virtually the entire extent of the section of the BMP2-treated culture, and, in addition, a small number of tubular structures are present (arrows). FIG. 9B shows a section through an hESC micromass culture treated with both BMP2 and TGF-β1 in which virtually all of the cells are surrounded by an Alcian blue cartilage matrix, and little, or no non-chondrogenic tissue is detectable. FIG. 9C shows a section through a BMP2+TGF-β1-treated hESC culture in which a small tubule (arrow) is present in addition to the extensive cartilage tissue. Such tubules constitute only a very small percentage of the BMP2+TGF-β1-treated cultures, and the vast majority of the culture undergoes cartilage differentiation. Table 1 shows that 88% of the cells present in the section of the day 14 BMP2-treated culture shown in FIG. 9A are surrounded by an Alcian blue positive matrix. In the sections of the BMP2 and TGFβ1-treated cultures shown in FIGS. 9B and C, 97.3% of the cells are surrounded by Alcian blue-positive matrix. These results demonstrate the substantial uniformity of chondrogenic differentiation by the BMP2 and BMP2/TGFβ1-treated hESC cultures in the method.

FIG. 11 (A) shows a day 14 control micromass culture of iPSC maintained without BMP2 supplementation. Little Alcian blue-positive matrix is present. FIG. 11 (B) shows a day 14 BMP2 treated iPSC micromass culture. Intense and widespread Alcian blue staining present throughout the extent of the culture.

FIGS. 12A-F are photomicrographs demonstrating the effect of iPSC dissociation method on chondrogenic differentiation in micromass culture as assayed by Alcian blue staining. FIG. 12 (D-F) shows iPSC cultures maintained in the absence of BMP2 in which little Alcian blue-positive matrix is present regardless of the dissociation method used.

FIG. 13A shows a day 14 micromass culture of iPSC maintained in the presence of BMP2. FIG. 13B shows a day 14 iPSC micromass culture maintained in the presence of a combination of BMP2 plus TGFβ1. FIG. 13C shows a day 14 iPSC micromass culture maintained in the absence of BMP2 or TGFβ1. Cultures supplemented with BMP2 or a combination of BMP2 and TGFβ1 accumulate comparable intense and widespread Alcian blue-positive matrix in contrast to iPSC micromass cultures which received no BMP2 supplementation which accumulate little Alcian blue-positive matrix.

FIGS. 14A-D are photomicrographs demonstrating the mouse articular cartilage damage model. FIG. 14A and FIG. 14C show frontal sections of a control unoperated mouse knee. The medial meniscus (mm) is indicated. FIG. 14B and FIG. 14D show frontal sections of a mouse knee 8 weeks following destabilization of the knee as a result of surgical ligament transection and partial meniscetomy. Absence of the medial meniscus is indicated by the asterisk. A localized region of articular cartilage damage is present (arrow).

FIG. 15A shows a control unoperated mouse digit tip in which bone is stained with Alizarin red. FIG. 15C shows a section through the control digit tip showing presence of soft and hard tissues. FIGS. 15B and 15D show a mouse digit tip amputated 6 weeks previously. All structures have undergone complete spontaneous regeneration.

FIG. 16A shows a living culture containing colonies with appearance characteristic of undifferentiated pluripotent stem cells (10×). FIG. 16B shows immunocytochemical staining for markers of pluripotent stem cells (SSEA-4 and Nanog) in the iPSCs.

DETAILED DESCRIPTION OF THE INVENTION

Figure 1:
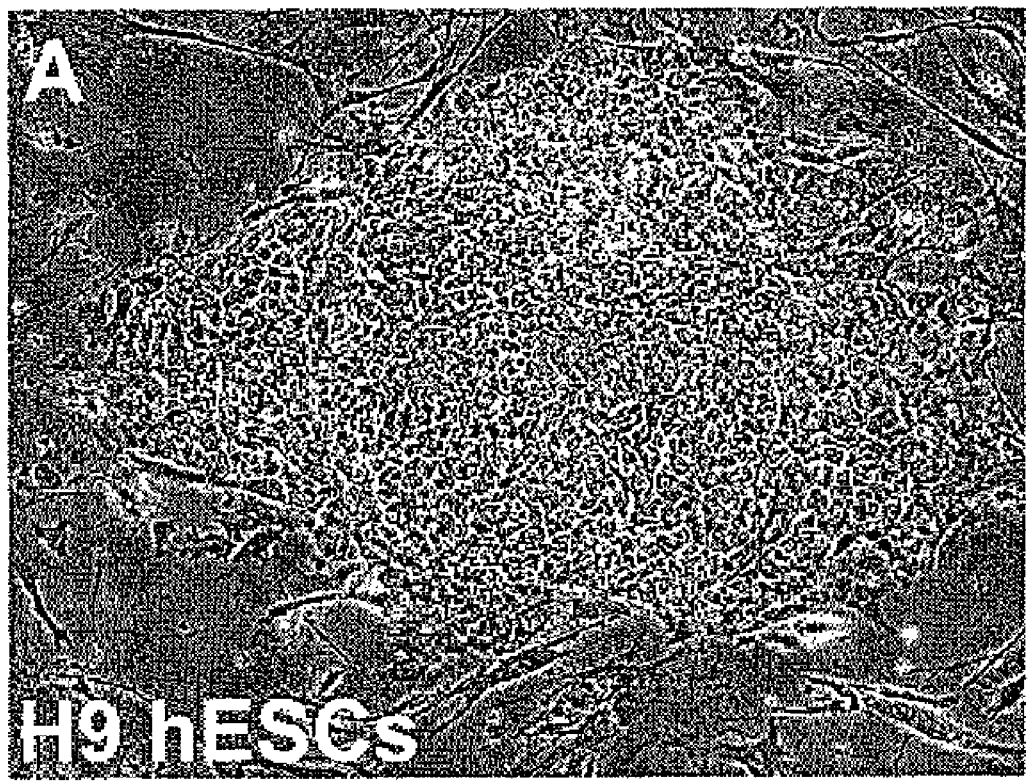
FIG. 1A is a photomicrograph showing a colony of undifferentiated pluripotent H9 human embryonic stem cells (hESCs) cultured on a feeder layer of irradiated mouse embryonic fibroblasts.
FIG. 1B is a photomicrograph showing embryoid bodies (EBs) derived from hESC colonies one day after their formation.
Figure 1:
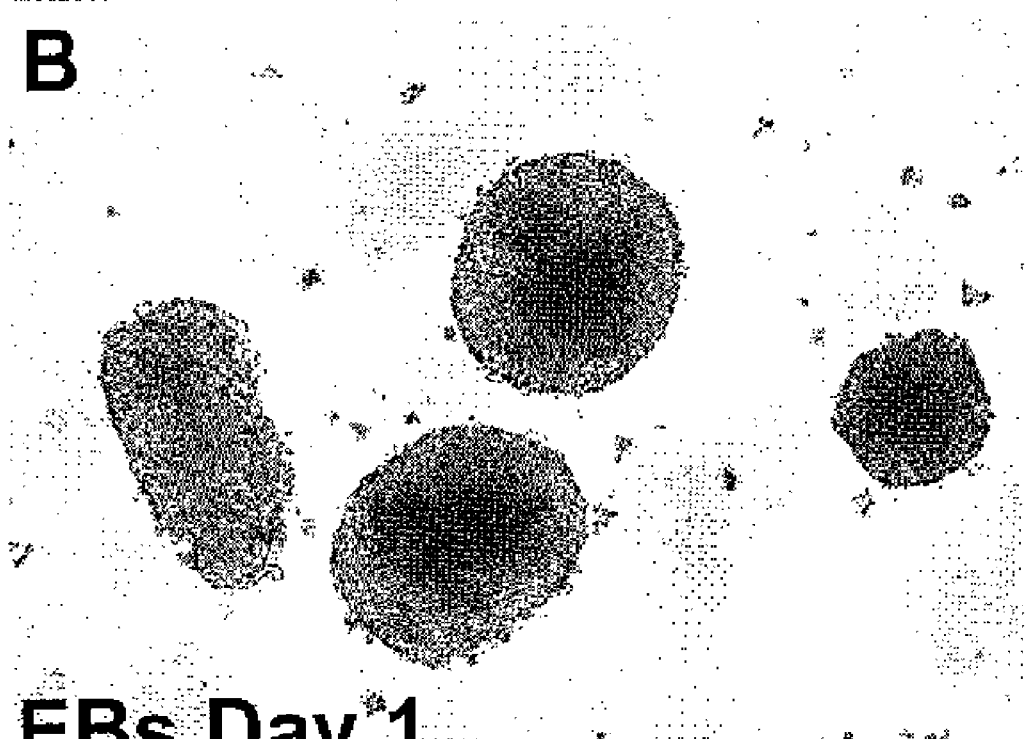
Figure 2:
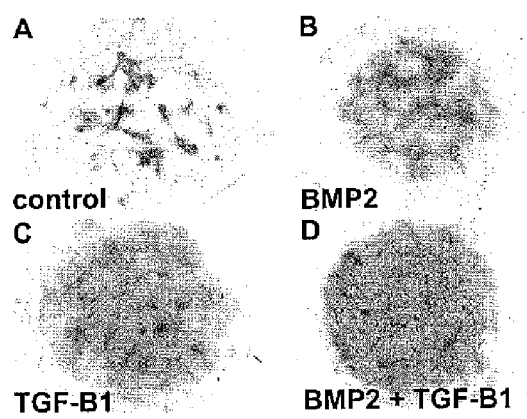
FIGS. 2A-D are photomicrographs showing Alcian blue stained day 21 micromass cultures established from the cells of EBs: (A) untreated control culture; (B) bone morphogenetic protein-2 (BMP2)-treated culture; (C) transforming growth factor_beta-1 (TGFβ1)-treated culture; and (D) culture treated with both BMP2 and TGFβ1.
Figure 3:
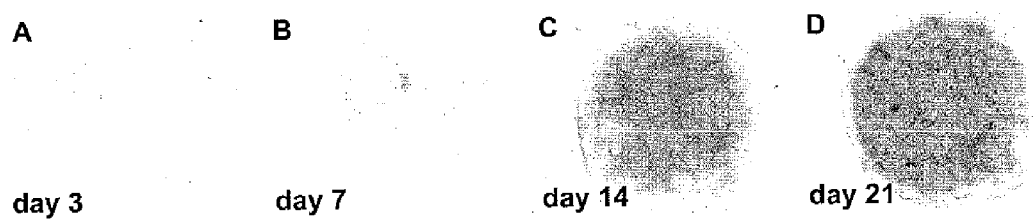
FIGS. 3A-D are photomicrographs showing a time course of Alcian blue matrix accumulation in EB cell micromass cultures treated with both BMP2 and TGFβ1.

Degenerative diseases of cartilage, e.g., osteoarthritis, are prevalent and debilitating chronic health problems and one of the main causes of decreased quality of life in adults (Magne D et al., 2005 Trends in Molecular Medicine, 11:519-526). Osteoarthritis (OA) is a non-inflammatory degenerative joint disease characterized by articular cartilage degradation and degeneration. OA affects most people over the age of 65, and it is estimated that 90% of the population over the age of 40 exhibits some form of cartilage degeneration in their joints resulting in pain and immobility (Song L et al., 2004 Cytotherapy, 6:596-601). Treatment of degenerative cartilage diseases is a particular challenge because of the limited capacity of the tissue for self-repair and renewal, making treatment of cartilage lesions a major clinical problem. Because of their unlimited capacity for self-renewal while maintaining the ability to differentiate into multiple cell types, human embryonic stem cells (hESCs) derived from the inner cell mass of the blastocyst are a powerful tool for the repair of cartilage defects using cell based tissue engineering therapies. Indeed, as described below, hESCs provide an unlimited supply of progenitor cells for cartilage repair.

Using hESCs for cartilage repair requires efficiently directing their differentiation into progenitor cells capable of participating in the repair of diseased cartilage. Prior to the invention, several culture systems had been developed in which ESC-derived cells differentiate to various degrees into chondrocytes (; Elisseeff J et al., 2005 Orthod Craniofac Res, 8:150-161; Harkness L et al., 2009 Stem Cell Rev 5; 353-368; Heng B C et al., 2004 Stem Cells, 22:1152-1167; Hoben G M et at 2009 Stem Cells Dev 18:283-292; Hwang N S et al., 2006 Stem Cells, 24:284-291; Hwang N S et al., 2006 Tissue Eng, 12:2695-2706; Jukes et al., 2008 Tissue Engineering Part A, 14:135-147; Kawaguchi J et al., 2005 Bone, 36:758-769; Koay E J et al., 2007 Stem Cells 25:2183-2190; Koay E J and Athanasiou K A 2009 tissue Eng Part A 15:2249-2257; Kramer J et al., 2000 Mechanisms of Development, 92:193-205; Kramer J et al., 2005 Cell Biology International, 29:139-146; Kramer J et al., 2005 Anat Embryol, 210:175-185; Ofek G et al., 2009 Biomech Eng 131: 061011; Sui Y P et al., 2003 Differentiation, 71:578-585; Toh W S et al., 2007 Stem Cells, 25:950-960; Toh W S et al., 2009 J Cell Mol Med 13B: 3570-3590; Vats A et al., 2006 Tissue Eng 12: 1687-1697; zur Nieden N I et al., 2005 BMC Dev Biol, 5:5-15). However, in these systems chondrocytes represented only a subpopulation of the cells that differentiate, complicating utilization of the cell population for cartilage repair.

Furthermore, most of the chondrogenic differentiation protocols utilize cells of embryoid bodies (EBs) derived from ESCs (Elisseeff J et al., 2005 Orthod Craniofac Res, 8:150-161; Harkness L et al., 2009 Stem Cell Rev 5: 353-368; Heng B C et al., 2004 Stem Cells, 22:1152-1167; Hoben G M et al 2009 Stem Cells Dev 18:283-292; Hwang N S et al., 2006 Stem Cells, 24:284-291; Hwang NS et al., 2006 Tissue Eng, 12:2695-2706; Jukes et al., 2008 Tissue Engineering Part A, 14:135-147; Kawaguchi J et al., 2005 Bone, 36:758-769; Koay EJ et al., 2007 Stem Cells 25:2183-2190; Koay EJ and Athanasiou KA 2009 tissue Eng Part A 15:2249-2257; Kramer J et al., 2000 Mechanisms of Development, 92:193-205; Kramer J et al., 2005 Cell Biology International, 29:139-146; Kramer J et al., 2005 Anat Embryol, 210:175-185; Ofek G et al., 2009 J Biomech Eng 131: 061011; Sui YP et al., 2003 Differentiation, 71:578-585; Toh WS et al., 2007 Stem Cells, 25:950-960; Toh WS et al., 2009 J Cell Mol Med 13B: 3570-3590; Vats A et al., 2006 Tissue Eng 12: 1687-1697; zur Nieden NI et al., 2005 BMC Dev Biol, 5:5-15; Waese and Stanford 2010 Stem Cell Res September 6). EBs are three-dimensional aggregates of cells formed by incubating suspensions of undifferentiated ESCs or colonies on non-adhesive substrates. The cells of EBs can differentiate into semi-organized tissues composed of cell types from all three germ layers of the embryo. The cellular environments and interactions that occur in EBs are difficult to precisely control, fostering cellular heterogeneity. Thus, utilizing EB-derived cells hinders the ability to obtain homogeneous populations of chondrogenic cells that can be used for tissue repair.

Some protocols have been reported in which the chondrogenic differentiation of hESCs without prior EB formation have been attempted. One protocol involved co-culturing the hESCs for an extensive period (several weeks) with differentiated bovine articular chondrocytes (Hwang NS et al., 2008 PLoS ONE, 3:1-10). Another protocol involved pre-culturing the ESCs in ill-defined conditioned medium from a hepatocarcinoma cell line (Hwang YS et al., 2008 Stem Cells Dev, 17:971-978) however this study resulted in limited and non-uniform chondrogenic differentiation (Hwang NS et al., 2008 PLoS ONE, 3:1-10).

Another study has utilized micromass cultures of mouse ES cells to attempt to obtain cartilage differentiation without prior EB formation (Yamashita A et al., 2009, Cell Death and Differentiation 16:278-286). The Yamashita protocol involved adding growth factors at the start of culture, and resulted in considerable cell death and detachment from the culture substrate. Moreover, the cultures exhibit only patchy and non uniform Alcian blue staining and little or no expression of the definitive cartilage marker aggrecan detectable by RT-PCR. The cultures were reported to express the hypertrophic cartilage marker collagen type 10 and undergo mineralization, indicating the cells in the culture have undergone hypertrophic chondrocyte maturation very early in the culture period. These characteristics represent a significant drawback to the method, because hypertrophic chondrocyte maturation is associated with osteoarthritis. The cultures were also reported to express the blood vessel marker flk1, indicating the heterogeneity of the culture. The relatively small amount of chondrogenic tissue that forms undergoes hypertrophic maturation, making it inappropriate for cartilage repair. Indeed a second study by the same authors (Yamashita A et al., 2010 PLoS One 5:e10998) reported that the cultures underwent further hypertrophy and ultimately formed bone-like tissue in vitro.

In contrast, the methods described herein yield substantially uniform chondrogenic differentiation as assayed by histological and molecular analyses. The methods yield cells that exhibit high level expression of aggrecan and other cartilage markers. The progressive differentiation that these cultures undergo enables us to obtain relatively pure populations of cells at discrete stages of differentiation that may be used for cartilage repair. Furthermore the cells do not undergo hypertrophic maturation, making them particularly attractive for cartilage repair.

These differences relate, in part, to the timing of growth factor addition. Yamashita added growth factors at the start of high density culture (zero time), whereas in the method described herein, the cultures receive growth factor after the 24 or 48 hours after establishment of high density culture. The timing of growth factor supplementation is critical for chondrogenic differentiation, as treatment of chondrogenic progenitors in micromass culture with BMP at the start of culture (time 0) causes cell death and inhibits chondrogenic differentiation (Fisher et al 2007) and others have shown that treatment of chondrogenic progenitors in vivo with BMP causes massive cell death (Macias et al 1997). The cultures also receive ROCK inhibitor to promote hESC survival (Watanabe K et al., 2007; Li X 2009). Suitable inhibitors include Y27632 and H1152 (both available from Calbiochem), AR-12286 (Aerie Pharmaceuticals), as well as HA-1100.HCl ([Hydroxyfasudil; 1-Hydroxy-5-isoquinolinesulfonyl)homo-piperazine], 3-(4-Pyridyl)-1H-indole, H-1152.2HCl ([H-1152P; (S)-(+)-2-Methyl-1-[(4-methyl-5-isoquinolinyl)sulfonyl]homopiperazine, and N-(4-Pyridyl)-N'-(2,4,6-trichlorophenyl) urea (the latter four of which are available from Alexis Biotchemicals).

Protocols for indirect differentiation of hESC into chondrocytes utilizing a mesenchymal stem cell-like intermediate have also been reported. However, several of these protocols utilize EBs to produce the mesenchymal stem cell-like intermediate (Lee E J et at, 2010 Tissue Eng A 16:705-717; Brown SE et al., 2008, Cells Tiss Org 189:256-260; Mahmood A et al., 2010 J Bone Min Res 25: 1216-1233; Hwang et al 2008; Cohen S et al., 2010 Tissue Eng A 16: 3119-3139; Harkness L et al., 2009 Stem Cell Rev 5: 353-368) which as discussed above, introduces cellular heterogeneity. Similarly, an EB step is used in a protocol reporting chondrogenic differentiation from a mesenchymal stem cell intermediate derived from human stem cells isolated from human gonadal ridge (hEG cells, Varghese S et al., 2010 Stem Cells 28: 765-774). Other protocols required co-culture with OP9 cells, a line of bone marrow derived mouse stromal cells (Barberi T et al., 2005 PLoS Med 2 e161) or coculture with human articular chondrocytes (Bigdeli N et al., 2009 Stem Cells 27:1812-1821) in order to produce the mesenchymal intermediate. Several protocols obtained the mesenchymal stem cell-like intermediate cell population through use of FACS sorting to identify hESC subpopulations expressing mesenchymal stem cell markers (Lian Q et al., 2007 Stem Cells 25:425-436; Kopher R A et al., 2010 Bone 47:718-728; Stavropoulos ME et at, 2009 Curr Prot Stem Cell Biol 9:1F.8.1-1F.8.10; Barberi T et al., 2005 PLoS Med 2 e161; Barberi T et al., 2007 Nature Med 13: 642-651) or through repeated passaging and extensive long term (several weeks) culture of the hESC at low density (Nakagawa T et al., 2009 Arthritis Rheum 60: 3686-3692; Arpornmeaklong P et at, 2009 Stem Cells Dev 18:955-968; Boyd NL et at, 2009 Tissue Eng A 15:1897-1908) in order to produce the spindle-shaped, fibroblast/mesenchymal-like cells which are then subjected to various chondrogenic differentiation protocols. However, in these protocols, chondrogenic differentiation obtained was non-uniform, as indicated by patchy immunostaining for collagen type II (Arpommeaklong P et at, 2009 Stem Cells Dev 18:955-968); lack of homogeneity of the tissue (Kopher et al 2010), non-uniform type II collagen and sox9 distribution (Barberi T et al., 2007 Nature Med 13: 642-651; Stavropoulos ME et at, 2009 Curr Prot Stem Cell Biol 9:1F.8.1-1F.8.10) formation of non-uniform, tissue with little Alcian blue staining (Lian Q et al., 2007 Stem Cells 25:425-436); and production of a poorly-characterized mass that detached from the culture plate (Boyd NL et al., 2009 Tissue Eng A 15:1897-1908). A protocol which subjected the hESC-derived mesenchymal fibroblast-like cells to pellet culture in the presence of BMP7 (Nakagawa T et al., 2009 Arthritis Rheum 60: 3686-3692) also produced non-uniform chondrogenic differentiation with the cultures exhibiting an extensive undifferentiated central core with chondrogenic differentiation being limited to cells at the periphery of the pellet. Chondrogenic differentiation in pellets treated with both BMP7 and TGFβ1 (Nakagawa T et at, 2009 Arthritis Rheum 60: 3686-3692) also was not uniform, with an undifferentiated central core and overall weak collagen type II immunostaining at the periphery. The expression of the definitive cartilage marker aggrecan by these cultures was not significantly increased relative to untreated control pellets.

The results of these earlier methods are in contrast to chondrogenic differentiation by hESC in methods described herein, which yield direct, progressive and substantially uniform cells. Another advantage is that the methods of the invention yield cells that are synchronized at discrete stages of differentiation. For example, cells are harvested at discrete points to obtain chondroprogenitors (2-3 day cells, characterized as just entering the cartilage lineage), early chondrocytes (day 4 cells, characterized as being in an early phase of chondrogenic differentiation), or fully differentiated chondrocytes (7-14 day cells have uniformly undergone overt differentiation into chondrocytes but have not undergone hypertrophic maturation).

| Cell population | Days of culture after high density culture establishment | Marker profile by qRT-PCR |
| --- | --- | --- |
| Chondroprogenitors | 2-3 | Moderate Brachyury, Sox9 and Col2a1. Low aggrecan. |
| Early chondrocytes | 4 | High Brachyury and Sox9, moderate aggrecan and Col2a1 |
| Fully differentiated chondrocytes | 7-14 | Low Brachyury and Sox9, high aggrecan and Col2a1. Col10a1 and OPN not detectable. |

Each of the cell populations described above are ideally suited for treatment of specific clinical conditions. For example, chondroprogentors (day 2-3 cells) are preferentially used for limb or finger regeneration, mensical or ligament repair, and fracture repair. Early chondrocytes (day 4 cells) are used for repair of articular cartilage defects due to injury, for repair or prevention of articular cartilage due to chronic degenerative disease (OA or RA), for regeneration and replacement of lost cartilage tissue due to trauma or congenital defect, for meniscal or fracture repair, and for repair of the fibrocartilage and cartilage of the temporomandibular joint. Fully differentiated chondrocytes are used for articular cartilage repair following acute or traumatic injury, or for repair or prevention of articular cartilage damage due to chronic OA or RA, as well as for fracture repair via endochondral ossification. Each stage is useful for modeling of cartilage development and differentiation, and iPSC derived cells in particular are useful for patient specific repair and regeneration, as well as for modeling of human disease, design and testing of targeted therapeutics, and for disease-specific repair of genetically compromised cartilage tissue.

Chondrogenic differentiation of iPSC has been reported (Medvedev S P et al., 2010 Stem Cells Dev October 17; Lian Q et al., 2010 Circulation 121:1113-1123). However, one protocol involved formation of EBs from the iPSC (Medvedev SP et al., 2010 Stem Cells Dev October 17); and the other protocol required sorting of the iPSC by fluorescence-activated cell sorting (FACS) to identify subpopulations expressing mesenchymal stem cell markers in order to obtain a mesenchymal stem cell-like intermediate cell population prior to induction of chondrogenic differentiation (Lian Q et al., 2010 Circulation 121:1113-1123). Chondrogenic differentiation in this protocol resulted in only about 60% of the cells being immunoreactive for collagen type II (Lian Q et al., 2010 Circulation 121:1113-1123). Yet another advantage of the present methods is the avoidance of the use of FACS (which is time-consuming and may introduce a risk of contamination).

The method described herein does not utilize EBs. The method does not involve coculture of hESCs or iPSCs with differentiated bovine articular chondrocytes, human articular chondrocytes, or mouse OP9 cells. The method does not involve pre- or co-culture with medium from hepatocarcinoma cells. Nor do the methods involve long-term passaging and culture in monolayer, or cell sorting via FACS. The methods are faster (less than 3 weeks, less than 2 weeks, or less than 1 week, e.g., cells enter chondrogenic lineages in as little as 2-3 days after establishment of high density cell cultures). The present method results in progressive, substantially uniform chondrogenic differentiation which enables production of populations of cells at discrete stages of differentiation for cartilage repair and other uses.

Described below are culture systems and conditions of the invention that promote the rapid, direct, progressive, and uniform differentiation of undifferentiated pluripotent hESCs into the chondrogenic lineage without prior embryoid body (EB) formation. Undifferentiated pluripotent hESCs and cells of embryoid bodies (EBs) derived from hESCs were subjected to the high density micromass culture conditions to direct the differentiation of embryonic limb bud mesenchymal cells into chondrocytes (Gay SW and Kosher R A, 1984 J Exp Zool, 232:317-326; Kosher RA et al., 1986 Dev Biol, 118; 112-117; Kosher RA et al., 1986 J Cell Biol, 102:1151-1156; Kulyk WM et al., 1991 Matrix, 11:282-288). The high density micromass culture system simulates the close juxtaposition of cells and cellular interactions that characterize the onset of the chondrogenic differentiation of mesenchymal progenitor cells in the developing embryonic limb. Micromass cultures of undifferentiated pluripotent hESCs treated with BMP2 alone (or the combination of BMP2 and TGFβ3 administered together) directly undergo progressive and substantially uniform (e.g., at least 88%) differentiation into the chondrogenic lineage without prior EB formation.

As an alternate approach to supplementation with BMP2 and TGFβ1, cultures are supplemented with other growth factors including bone-morphogenetic protein-4 (BMP4, NG_009215 (GI:219521814), incorporated herein by reference); bone morphogenetic protein-7 (BMP7, NM_001719 (GI:187608319), incorporated herein by reference); growth and differentiation factor-5 (GDF5, NG_008076 (GI: 193083169), incorporated herein by reference); transforming growth factor beta-3 (TGFβ3, NG_011715 (GI:225735563), incorporated herein by reference); or insulin like growth factor-1 (IGF-I, NG_011713 (GI:225735562), incorporated herein by reference). Each of these factors promote differentiation into the chondrogenic lineage (Waese E Y and Stanford W L 2010 Stem Cell Res September 6; Nakagawa T et al., 2009 Arthritis Rheum 60: 3686-3692; An C et al., 2010 Ann Biomed Eng 38: 1647-1654; Moore Y R et al., 2010 J Clin Periodontol 37: 288-298).

As an alternate approach to micromass culture, hESC are subjected to pellet culture. In this method, dissociated hESC or iPSC (approximately $1\times10^5$-$1\times10^7$ cells) are pelleted in a microfuge tube. The pellet is then subjected to the same chondrogenic differentiation protocols as described above for micromass culture. Growth factor (s) are added to the pellet and diffuse into the pellet to induce differentiation of the cells. The pellet itself is then used for implantation, infusion or other means of administration to a joint or joint space or other repair tissue for therapy. This protocol also achieves direct, progressive and substantially uniform chondrogenic differentiation of hESC without EB formation. The pellet culture protocol is also used to direct the differentiation of iPSC into the chondrogenic lineage.

Cell Culture Systems: System I and System II

Figure 17:
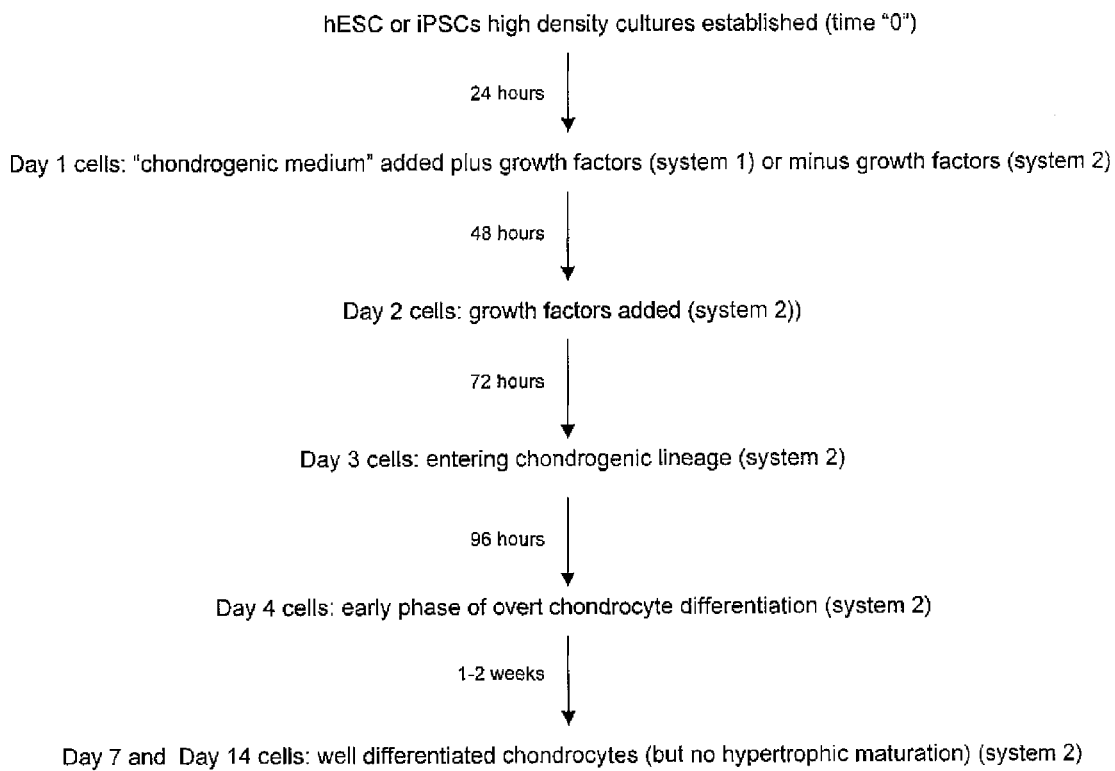
FIG. 17 is a flow diagram showing the steps for producing chondrogenic cells from undifferentiated human embryonic stem cells or from induced human pluripotent stem cells.

The cells are prepared using one of two systems. In system I, high density cultures are established and cultured for 24 hours at which point chondrogenic medium containing BMP2 or the combination of BMP2 and TGFβ is added to the cells. In system II, high density cultures are established and cultured for 24 hours at which point chondrogenic medium without growth factor(s) is added to the cells. At the beginning of the $3^{rd}$ day, BMP2 or the combination of BMP2 and TGFβ is added to the cells. One day later (at the end of day 3), the cells substantially uniformly enter the chondrogenic lineage as evidenced by gene expression profiles and physical characteristics/histology. A flow chart illustrating the timing of culture, growth factor addition, and stage of differentiation is shown in FIG. 17.

As described below, the gene expression profiles of hESC-derived cells harvested at various times during the progression of their differentiation enabled the identification of cells in different phases of the chondrogenic lineage ranging from cells just entering the chondrogenic lineage to overtly differentiated chondrocytes. The methods described herein enable analysis of the ability of hESC-derived progenitor cells in different phases of chondrogenic lineage to repair cartilage using cell-based tissue engineering therapies. The uniform and progressive chondrogenic differentiation that occurs also facilitates the identification of genes, signals, and regulatory networks involved in the progressive conversion of undifferentiated pluripotent hESCs into progenitor cells determined to differentiate into the chondrogenic lineage.

Methods of Therapy

Approaches for administering the cells include direct implantation of the micromass or pellet cultures into the damaged area via surgical means, such as open knee surgery as for autologous chondrocyte implantation (ACI, Zazlav K et al., 2009 Am J Sports Med, 37:42-55) or arthroscopically in a scaffold-free approach (Jubel A et al., 2008 Am J Sports Med 36: 1555-1564; Erggelet C et al 2003 Arthroscopy 19: 108-110). In some procedures, the cultures are also dissociated by collagenase digestion or other means, and cells seeded into scaffolds or other supports. Such supports include collagen membranes (e.g. Chondrogide), hyaluronan-containing matrices (e.g. Hyaff-11), polyglactin fleece or other matrices. The cell-seeded matrices are then either surgically implanted (Kon et al., 2009 Am J Sports Med 37: 156S-166S) as for matrix-induced autologous chondrocyte repair (MACI) (Brittberg, 2010 Am J Sports Med, 38: 1259-1271) or HyalgraftC (Gobbi A et al., 2006: Am J Sports Med 34: 1763-1773); or implanted via arthroscopy (Gianni E et al., 2008 Am J Sports Med 36:873-880; Nixon AJ 2002 Clinical Tech Equine Practice 1: 257-269). The dissociated cells are also encapsulated in collagen, chitosan, agarose or hyaluronan-containing gels and the cell-gel mixture used to fill the damaged region in a surgical procedure (Funayama A et al., 2008 J Orthop Surg 13: 225-232; Hoemann C et al., 2005 OsteoArthritis Cart 13: 318-329; Emans PJ et al., 2010 PNAS 107:3418-3423). In these methods, the concentration of cells to be used is between ($1\times10^6$-$2\times10^7$ cells/ml).

Alternately, the dissociated cells are injected or infused into the knee via direct intra-articular injection in a non-invasive manner. The number of cells to be introduced is between ($1\times10^6$-$2\times10^7$ cells/ml). The cells are injected in saline as for introduction of autologous mesenchymal stem cells (MSC) into the injured or arthritic knee (Centeno CJ et al., 2008 Pain Physician 11: 343-353) or injection of MSC into joints of rats, pigs and goats with cartilage damage (Horie M et al., 2009 Stem Cells 27:878-887; Lee KB et al., 2007 Stem Cells 25:2964-2971; Murphy JM et al., 2003 Arthritis Rheum 48:3464-3474). In another approach, cells are injected in conjunction with other substances including hyaluronan preparations used for viscosupplementation (e.g. Synvisc, Supartz) which alleviate clinical arthritis pain and immmobility (Petrella RJ and Petrella M 2006, J Rheumatol 33: 951-956; Brander VA and Stadler T S 2009 Phys Sports Med 37: 38-48); or in conjunction with growth factors such as BMP7 which delay osteoarthritic progression (Hunter DJ et al., 2010, BMC Musculoskelet Disord 11: 232; Hayashi M et al., 2010 J Orthop Res 28: 1502-1506).

One approach to cell delivery is arthroscopic administration. In some cases, the cells are administered or implanted before, after or during a surgical or arthroscopic procedure to repair an associated defect or condition, e.g., cells are administered to a joint space in conjunction with an ACL repair procedure, meniscus repair, rotator cuff repair, or other procedure. This approach has been used to evaluate repair of meniscal injury by mesenchymal stem cells in animals (Horie M et al., 2009 Stem Cells 27:878-887) and is suitable for humans (Centano C J et al., 2008 Med Hypotheses 71:900-908.)

The cells and methods are useful to assist in repair of sports-related, combat-related and other traumatic injuries to bones, cartilage and limbs (Goldstein 2006 J Am Acad Orthop Surg 14: S152-156; Sundelacruz S and Kaplan DL 2009 Sem Cell Dev Biol 20: 646-655). The cells are useful for repair of long bone fractures, which repair via endochondral ossification, a process which recapitulates the normal developmental sequence involving ossification on a cartilage template (Kronenberg HM 2003 Nature 423: 332-336). Cells are introduced into the region of the fracture by injection or implantation, and undergo remodeling to form bone for repair, as described in methods utilizing mesenchymal stem cells (Kallai I et al., 2010 J Biomech 43: 2315-2320; Scotti C et al., 2009 PNAS 107: 7251-7256).

The cells are also useful in methods of regenerating fingers or limbs lost to traumatic injury due to accident or military conflict, or congenital defect. Lower animals including newts and frogs possess the ability to regenerate limbs, but this ability is largely lost in adult mammals (Muller TL et al., 1999 Sem Cell Dev Biol 10: 405-413) due to insufficient cells and signals required to carry out a regeneration response (Gurtner GC et al., 2007 Ann Rev Med 58:299-312; Muneoka K et al., 2008 Sci Am 298:56-63).

A murine model of limb regeneration was established. In this model, distally amputated digits undergo a spontaneous regeneration response, whereas proximally amputated digits fail to regenerate (Han Met al., 2008 Dev Biol 315: 125-135). This model provides a system for testing the ability of hESC and iPSC derived chondroprogenitor cells, particularly cells just entering the skeletal and chondrogenic lineage (e.g. day 2, day 3 or day 4 cells) to participate in or promote limb regeneration in a mammal. Methods of delivery for therapy for regeneration of limbs (arms or legs, hands or feet) or digits (fingers or toes) include introduction of the cells produced by the method into the digit or limb by injection or implantation. Cells are introduced in scaffolds or gels with or without growth factors. The digit regeneration model is described in FIGS. 15A-D.

Disease Models iPSC obtained from patients with genetic diseases are used for in vitro modeling of human disease and as a system for design and testing of targeted therapeutics (Amabile G and Meissner A 2009 Trends Molec Med 15: 59-68; Laustriat D et al., 2010 Biochem Soc Trans 38: 1051-1057). The invention is also useful for in vitro modeling of genetic cartilage diseases and for design and testing of therapeutics. These disorders which include chondrodysplasia and achondoplasia cause disfiguring and disabling short stature and even death (Krakow D and Rimoin D 2010 Genet Med 12: 327-341). For this purpose, iPSC are derived from fibroblasts or other cell types obtained from individuals with genetic disorders affecting cartilage (e.g., chondrodysplasia, achondroplasia or others) and the method described herein is applied to induce chondrogenic differentiation. The iPSC derived chondrogenic cells recapitulate the disease process in vitro, enabling mechanistic study of disease pathology and design and testing of targeted therapeutics. The approach extends to chondrodysplasias in which mechanisms are largely unknown (Krakow D and Rimoin D 2010 Genet Med 12: 327-341), such as those caused by defects in extracellular matrix protein synthesis or sulfation; metabolic enzymes, ion channels or transporters; macromolecular folding, processing or degradation; hormones, growth factors, receptors, or signal transducers; transcription factors; RNA processing; or cytoskeletal proteins. The approach is applied to gene profiling to identify new genes important in normal or abnormal cartilage function or new targets for therapy (Pogue R et al., 2004 Matrix Biol 23: 299-307). The approach may be combined with gene targeting to attempt patient specific cell-mediated therapy of mongenic chondrodysplasias (Wong G K and Chiu AT 2010 Biotechnol Adv July 24).

Experimental models in large and small animals are used to evaluate cartilage repair (Chu CR et al., 2010 Tissue Eng Part B 16: 105-115). In one model, the knee joint is de-stabilized by surgical disruption of the knee ligaments and/or partial meniscetomy, which results in inappropriate focused weight bearing and causes localized articular cartilage destruction. The cartilage defect produced in this model is highly reproducible and the onset and progression of cartilage destruction faithfully replicates what is seen in chronic human osteoarthritis. This model has been used to evaluate cell-mediated repair of damaged articular cartilage by mesenchymal stem cells injected into the joint of various animals (e.g. Murphy JM et al., 2003 Arthritis Rheum 48:3464-3474; Kubo S et al., 2009 Arthritis Rheum 60: 155-165). This model has been extended to rodents (Kamekura S et al., 2005 Osteoarthritis Cart 13: 632-641; Glasson SS et al., 2007 Osteoarthritis Cart 15:1061-1069; Welch ID et al., 2009 Arthritis Res Ther 11:R14). This model has now been established in immune-compromised mice for use in testing in vivo repair by the hESC and iPSC derived chondrogenic cells (FIGS. 14A-D).

Another model used to evaluate cartilage repair utilizes surgically generated articular cartilage defects (Ahern BJ et al., 2009 Osteoarthritis Cart 17: 705-713). In this model the non-loading region of the patellar groove of the femur is exposed, and a full-thickness defect is mechanically created by carving a groove or punching out a hole extending from the cartilage surface to the subchondral bone. This approach is used for large animals and has also been adapted to the rat (Dausse Y et al., 2003 Osteoarthrtis Cart 11: 16-28) and mouse (Eltawil NM et al., 2009 Osteoarthritis Cart 17:695-704; Osteoarthritis Cart 6: 695-704). This model simulates articular cartilage damage following acute injury, and as in humans, failure to heal the defect leads to further cartilage degeneration outside the damaged region and overt OA.

EXAMPLE 1

Culture of hESCs and Embryoid Body Formation

The H9 hESC line generated at the WiCell Research Institute (Thomson J A et al., 1998 Science, 282:1145-1147). The H9 cells were cultured in the serum-free hESC medium previously described (Toh W S et al., 2007 Stem Cells, 25:950-960) on a feeder layer of irradiated CF1 mouse embryonic fibroblasts (MEFs) (see, FIG. 1A) prepared using standard protocols by the University of Connecticut Stem Cell Core. Colonies were passaged every 4-6 days after treatment with 1 mg/ml collagenase IV (Invitrogen). hESCs from passage numbers 36 to 45 were used in these studies.

To generate EBs, hESC colonies were detached from the MEF feeder layers by treatment with 0.1% dispase (Invitrogen) for 20-30 minutes at 37° C., suspended in EB formation medium (Toh WS et al., 2007 Stem Cells, 25:950-960) in T75 Ultra-Low Attachment Flasks (Corning, Lowell, Mass.), and incubated for 5 days. Media was changed every 48 hours. The suspended hESC colonies form EBs consisting of three-dimensional aggregates of cells as shown in FIG. 1B.
Preparation of Micromass Cultures from Eb Cells and from Undifferentiated Hescs Micromass cultures were prepared from dissociated cells of both day 5 EBs (FIG. 1B) and undifferentiated hESC colonies (FIG. 1A). Prior to dissociation, hESC colonies were detached from the MEF feeder layer as described above. The detached hESC colonies and EBs were dissociated into single cells with 0.05% trypsin/EDTA (Invitrogen), followed by passage of the cell suspension through a 40 µm cell strainer (BD Biosciences, Franklin lakes, NJ). The dissociated cells were suspended at $2 \times 10^7$ cells/ml in high-glucose DMEM supplemented with 10% FBS (FBS, Hyclone) and 10% KSR. Micromass cultures were prepared by spotting 10 µl of the cell suspensions ($2 \times 10^5$ cells) in each well of 24-well tissue culture dishes (Nunc; Fisher). After a two hour incubation at 37° C. in a humidified 5% $CO_2$ incubator to facilitate cell attachment, 0.5 ml of the same medium was added to each well. After 24 hours (the beginning of day 2 of culture) the medium was removed and the cultures supplied with the serum-free chondrogenic medium (Toh W S et al., 2007 Stem Cells, 25:950-960). Chondrogenic medium contains high-glucose DMEM supplemented with ITS (6.25 µg/ml insulin, 6.25 µg/ml transferrin, 6.25 µg/ml selenium), 1.25 mg/ml bovine serum albumin, 5.35 µg/ml linoleic acid (BD Biosciences), 1% KSR, 40 µg/mL-proline (Sigma-Aldrich), 50 µg/ml ascorbic acid 2-phosphate (Sigma-Aldrich), 1% nonessential amino acids (Invitrogen), 10-7 M dexamethasone (Sigma-Aldrich), and 100 units/100 µg penicillin/streptomycin (Invitrogen). The cells are then cultured in the presence or absence of either 100 ng/ml recombinant human BMP2 (R&D Systems, Minneapolis), 10 ng/ml of recombinant human TGF-β1 (R&D Systems, Minneapolis), or a combination of 100 ng/ml of recombinant human BMP2 plus 10 ng/ml of recombinant human TGF-β1. In some experiments, hESC micromass cultures were cultured for 24 hours (throughout day 2) in chondrogenic medium lacking growth factors, after which (at the beginning of day 3 of culture) they were supplied with fresh chondrogenic medium supplemented with growth factors as described above. Media including growth factors was changed every 48 hours throughout the culture period.

Alcian Blue Staining, Type II Collagen and Aggrecan Immunostaining

The accumulation of cartilage matrix was monitored histochemically by staining micromass cultures with Alcian blue, pH 1.0 as previously described (Gay S W and Kosher R A, 1984 J Exp Zool, 232:317-326). For immunostaining of type II collagen, micromass cultures were fixed for 30 minutes in 4% paraformaldehyde in phosphate buffered saline (PBS), washed in PBS, scraped off the tissue culture plate, dehydrated, embedded in paraffin, and sectioned sagitally at 7 µM. Immunohistochemistry was performed using a Vectastain Elite ABC kit (Vector, Burlingame, Calif.) and a monoclonal antibody against type II collagen (anti-collagen Type II, clone 6B3; Chemicon) and a monoclonal antibody against the interglobular domain of the cartilage marker, aggrecan (6-B-4; Abeam). Sections were de-paraffinized, quenched in 0.5% $H_2O_2$ in methanol for 15 minutes, and antigen retrieval was performed by incubation with pepsin (Labvision). Sections were blocked with 5% normal horse serum in TBS, and then incubated for 1 hour with the type II collagen antibody diluted 1:200. The sections were then incubated for 1 hour at room temperature with biotinylated horse anti-mouse IgG diluted 1:200, treated with an avidin-biotin horseradish peroxidase complex (Vectastain ABC kit), and developed with diaminobenzidine/$H_2O_2$ (Vector). Negative controls were not incubated with the primary antibody, and exhibited little or no staining.
Real Time Reverse Transcription-Polymerase Chain Reaction (Real Time RT-PCR)

Total RNA was extracted from micromass cultures using the Qiagen RNeasy Mini kit (Qiagen, Chatsworth, Calif.), and treated with RNase-free DNase (Ambion, Austin, Tex.) to eliminate possible genomic DNA contamination. Two µg of RNA per 20 µl of reaction volume were reverse transcribed into cDNA using the High Capacity cDNA Reverse Transcription Kit (Applied Biosystems, Foster City, Calif.). Real-time RT-PCR was performed using the ABI Prism 7900 Sequence Detection System, TaqMan Gene Expression Master Mix, and TaqMan Gene Expression Assays (Applied Biosystems) for Sox9 (assay ID Hs00165814_m1), aggrecan (assay ID Hs00153936_m1), type II collagen (Col2a1) (assay ID Hs00264051_m1), type X collagen (Col10a1) (assay ID Hs00166657_m1), osteopontin (opn) (assay ID Hs00960942_m1), Indian hedgehog (Ihh) (assay ID Hs01081801_m1), Brachyury (assay ID Hs00610080_m1), and glyeraldehyde-3-phosphate dehydrogenase) (GAPDH) (Hs99999905_m1). Gene expression levels were determined by the ΔΔCt method using GAPDH as the internal reference gene. Relative quantities of each gene were calculated as $-2^{\Delta\Delta Ct}$ in duplicate samples prepared from each of 2-3 independent micromass cultures for each treatment and time point analyzed. Thermal cycling conditions were 50° C. for 2 minutes, 95° C. for 10 minutes followed by 40 cycles of 15 second denaturation at 94° C. and 1 minute extension at 60° C.

EXAMPLE 2

Direct and Progressive Chondrogenic Differentiation of Undifferentiated Pluripotent hESCs In view of the ill-defined cellular environments and inherent cellular heterogeneity characteristic of EBs, the ability of undifferentiated pluripotent H9 hESCs (FIG. 1A) to directly differentiate into the chondrogenic lineage when subjected to high density culture was examined. High density cultures are characterized by a concentration of greater than $1 \times 10^5$ cells per 10 µl of medium. For example, the concentration of cells is in the range of 1-4×10$^5$ cells per 10 µl of medium, e.g., 2×10$^5$ cells per 10 µl. The volumes are scaled up as desired for larger scale cultures provided that the cell density/ratio remains in the range described above.

One day after their establishment, micromass cultures of dissociated H9 cells were supplied with serum-free "chondrogenic medium" in the presence and absence of 100 ng/ml of BMP2. As shown in FIG. 4A, only a few small Alcian blue staining areas were present in day 14 untreated micromass cultures established directly from dissociated undifferentiated H9 hESCs cells. In the presence of exogenous BMP2, virtually uniform intensely staining Alcian blue-positive matrix accumulates in the day 14 BMP2-treated hESC micromass cultures (FIG. 4B). In addition to uniform Alcian blue staining, cartilage-characteristic type II collagen detectable by immunostaining with a type II collagen antibody was present throughout the extent of BMP2-treated cultures (FIG. 4C).

The progression of accumulation of Alcian blue matrix by micromass cultures of undifferentiated H9 cells cultured as described above is shown in FIG. 5A-C. Little Alcian blue staining was detectable after 3 days of culture (FIG. 5A), but by day 7 relatively uniform Alcian blue staining was detectable throughout the culture (FIG. 5B). At day 14, more intensely staining Alcian blue-positive matrix was present throughout the entirety of the culture (FIG. 5C). These results indicate that undifferentiated pluripotent hESCs directly and quite uniformly undergo chondrogenesis when provided with the appropriate cellular environment (high density micromass culture) and exogenous signaling molecules such as BMP2 without the necessity of passing through an EB stage.

A modification of the chondrogenic differentiation protocol described above further enhances the progression of the differentiation of hESCs into the chondrogenic lineage. In this modified protocol, one day after being established, the hESC micromass cultures are supplied with serum-free "chondrogenic medium" lacking BMP2, and then 24 hours later supplied with 100 ng/ml of BMP2. As shown in FIG. 5D-F, although little Alcian blue positive matrix was detectable in day 3 cultures, uniform and fairly intense Alcian blue matrix was present throughout the extent of day 7 cultures. By day 14, a very intensely staining Alcian blue matrix was present throughout the entirety of the cultures (FIG. 5F). The extent and intensity of Alcian blue staining was greater utilizing this modified protocol in which exogenous BMP2 was provided on day 3 (FIGS. 5D-F) than in the protocol in which the hESC cultures were supplemented BMP2 on day 2 (FIG. 5A-C).

EXAMPLE 3

Characterization of Cells in Various Phases of the Chondrogenic Lineage in hESC Micromass Cultures by Gene Expression Profiling To confirm and quantify the progression of the differentiation of pluripotent hESCs into the chondrogenic lineage and to further characterize progenitor cells in different phases of the lineage, the expression of marker genes characteristic of different stages of the chondrogenic lineage was examined by quantitative Real Time RT-PCR. Gene expression patterns were analyzed at various times in BMP2-treated micromass cultures of pluripotent hESCs subjected to the modified chondrogenic differentiation protocol that leads to the progressive chondrogenic differentiation assayed by Alcian blue matrix staining as shown in FIGS. 5D-F above.

Figure 7:
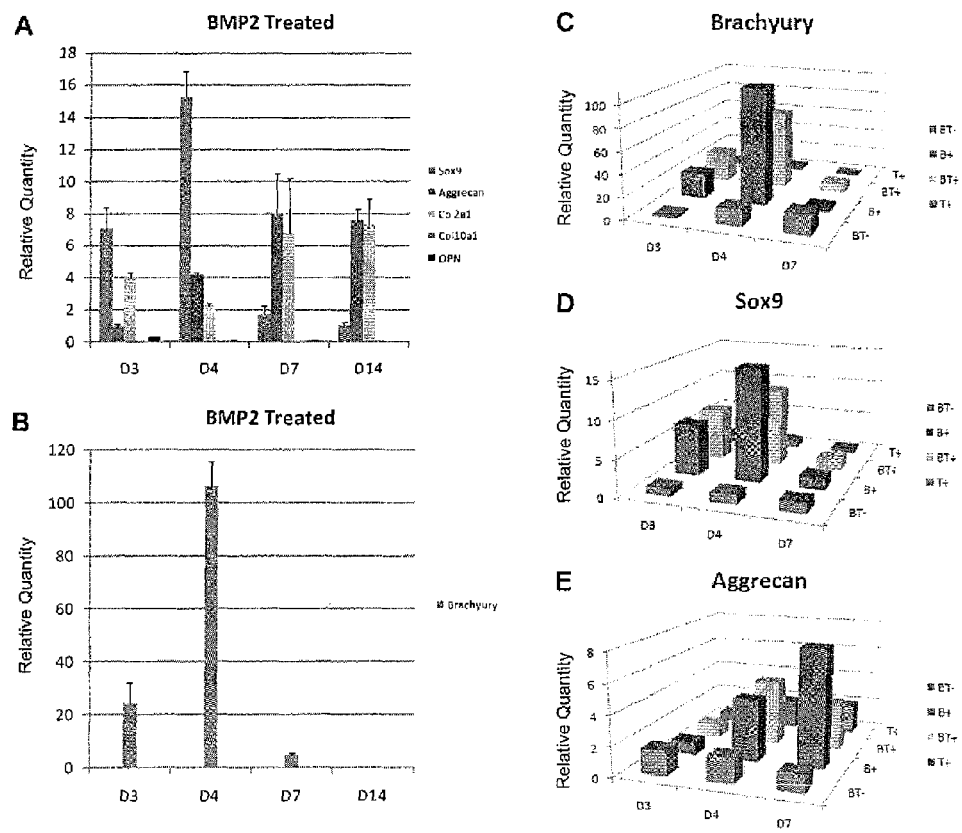
FIGS. 7A-E are bar graphs showing Sox9, aggrecan, Col2a1, Col10a1, and osteopontin (OPN) (A) and Brachyury (B) transcript expression in day 3 (D3), day 4 (D4), day 7 (D7), and day 14 (D14) hESC micromass cultures supplied with BMP2 at 48 hours of culture as determined by quantitative Real Time RT-PCR. Expression levels were determined by the ΔΔCt method using GAPDH as endogenous control. Relative quantities were calculated as $-2^{\Delta\Delta Ct}$, and normalized to expression levels at day 2 which were set to a value of 1. Values are the means of 3 (±SEM) (days 4, 7, and 14) or 2 (±range) (day 3) determinations. (C-E) Expression levels of Brachyury (C), Sox9 (D), and aggrecan (E) in day 3 (D3), day 4 (D4), and day 7 (D7) untreated control (BT−, blue), BMP2-treated (B+, red), BMP2 plus TGFβ1-treated (BT+, green), and TGFβ1-treated (T+, purple) hESC micromass cultures.
Figure 8:
FIG. 8 is a photomicrograph of a section through a day 14 BMP2-treated culture immunostained with an antibody against the interglobular domain of aggrecan. Cells which exhibit intracellular aggrecan staining are present throughout the extent of the culture. This indicates that virtually all of the cells that are surrounded by a type II collagen extracellular matrix (as shown in FIGS. 4A-C) are expressing the cartilage marker aggrecan as assayed by immunostaining with a cell autonomous marker.

As shown in FIG. 7A, at the end of day 3 of culture, which is 24 hours after the addition of exogenous BMP2, there is a striking 7-fold upregulation in the expression of the chondrogenic transcription factor Sox9. Sox9 has been characterized as a "master regulatory gene" for cartilage differentiation, and is a critical regulator of virtually of all the early phases of chondrogenesis (Akiyama H et al., 2002 Genes and Development 16:2813-2828; Lefebvre V and Smits P, 2005 Birth Defects Res C Embryo Today, 75:200-212). Thus, the striking upregulation of Sox9 expression in day 3 cultures is consistent with the entrance of the cells into the chondrogenic lineage. It is also noteworthy that the day 3 cultures exhibit a 24-fold upregulation in the expression of the transcription factor Brachyury (FIG. 7B). Brachyury is a marker of the mesodermal lineage and is also expressed by the prechondrogenic mesodermal cells that will give rise to cartilage in the developing limb (Herrmann B G, 1995 Seminars in Developmental Biology, 6:385-394; Hoffmann A et al., 2002 J Cell Sci, 115:769-781; Liu C et al., 2003 Development, 130:1327-1337). Thus, the upregulated expression of Brachyury along with Sox9 further indicates that day 3 cultures have entered into the chondrogenic lineage. Although day 3 cultures exhibit upregulated expression of Sox9 and Brachyury, the cultures do not exhibit upregulated expression of the cartilage marker aggrecan (FIG. 7A). In day 3 cultures, aggrecan is expressed at the same low basal level as it is at day 2. Aggrecan is the major sulfated proteoglycan of cartilage matrix and is a definitive highly specific molecular marker of overtly differentiated chondrocytes (Han Y and Lefebvre V, 2008 Molecular and Cellular Biology, 28:4999-5013). These results indicate that although day 3 cultures are entering into the chondrogenic lineage, they have not yet undergone overt differentiation into chondrocytes. It should also be noted that although day 3 cultures do not exhibit upregulated aggrecan expression, they do exhibit about a 4-fold upregulation in expression of transcripts for Col2a1 which encodes cartilage-characteristic type II collagen (FIG. 7A). However, unlike aggrecan, Col2a1 is expressed by prechondrogenic mesenchymal cells at an early stage in the chondrogenic lineage in the developing limb, as well as by differentiated chondrocytes (Han Y and Lefebvre V, 2008 Molecular and Cellular Biology, 28:4999-5013; Nah H D and Upholt W B, 1991 J Biol Chem, 266:23446-23452; Sakai K et al., 2001 Matrix Biol, 19:761-767). The gene expression patterns indicate that day 3 cultures are entering into the chondrogenic lineage, but have not yet undergone overt differentiation into chondrocytes.

As shown in FIGS. 7A and 7B, day 4 cultures exhibit further upregulation in the expression of the transcriptional regulators Sox9 and Brachyury. Sox9 expression is more than 2-fold higher and Brachyury expression is 5-fold higher in day 4 cultures than in day 3 cultures (FIGS. 7A and 7B). Moreover, day 4 cultures exhibit a greater than 4-fold upregulation in the expression of the definitive cartilage marker aggrecan (FIG. 7A). The upregulated expression of aggrecan indicates that the day 4 cultures are in an early phase of overt differentiation into chondrocytes.

By day 7 of culture, the expression of Sox9 and Brachyury are strikingly down-regulated (FIGS. 7A and 7B). On day 7, the expression of Sox9 is decreased about 10-fold (FIG. 7A) and Brachyury expression about 24-fold (FIG. 7B) compared to day 4. By day 14, Sox9 expression continues to decline to very low levels and the expression of Brachyury on day 14 is negligible (FIGS. 7A and 7B). The downregulation of Sox9 and Brachyury expression on day 7 and 14 is accompanied by an about 8-fold upregulation in the expression of the cartilage markers aggrecan and Col2a1. As described above, the upregulation of aggrecan and Col2a1 expression at days 7 and 14 correlates with the uniform accumulation of Alcian blue positive matrix and type II collagen detectable by immunostaining. These gene expression and staining patterns indicate that day 7 and 14 cultures have quite uniformly undergone overt differentiation into chondrocytes.

Significantly, the day 7 and 14 cultures which have undergone overt cartilage differentiation do not express markers of hypertrophic chondrocyte maturation. No expression of Col10a1, a definitive molecular marker of hypertrophic chondrocytes, is detectable in day 7 or day 14 cultures, and expression of osteopontin (OPN), a marker of terminal hypertrophic maturation is negligible (FIG. 7A). Day 7 and 14 cultures also exhibit negligible expression of Indian hedgehog (Ihh), a marker of prehypertrophic chondrocytes that have initiated maturation. These results indicate that the chondrocytes comprising day 7 and 14 cultures have not undergone hypertrophic chondrocyte maturation.

Inappropriate hypertrophic maturation is a hallmark of osteoarthritis; thus, the presence of this phenotype in the cell populations to be used for human (or other mammalian) therapy is undesirable. In some systems, chondrogenic cultures induced by BMPs show high expression of genes associated with chondrocyte hypertrophy including collagen type (COL) X and Indian hedgehog (1HH). Such hypertrophy-associated changes are found in pathological conditions such as osteoarthritis. The absence or negligible expression of such hypertrophy-associated markers is an indication that the cells described herein possess advantages over other preparations and are ideally suited for therapeutic administration to diseased or damaged cartilaginous joint tissues.

As shown in FIGS. 7C-7E, the expression of cartilage lineage markers in hESC micromass cultures treated with BMP2 alone were compared to expression in cultures treated with TGFβ1 alone or treated with a combination of TGFβ1 and BMP2. Unlike BMP2, TGFβ1 alone does not stimulate the expression of cartilage markers. Indeed, TGFβ1-treated cultures and untreated control cultures exhibit comparable low levels of expression of aggrecan, Sox9, and Brachyury (FIGS. 7C-7E).

EXAMPLE 4

Differentiation of Undifferentiated Pluripotent hESCs/Direct And Progressive Differentiation Of Undifferentiated Pluripotent hESCs Into Progenitor Cells In Various Phases Of The Chondrogenic Lineage Fulfilling the potential of hESCs for treatment of degenerative diseases of cartilage such as osteoarthritis requires developing methods for directing their differentiation into the chondrogenic lineage. Described above are culture systems and conditions that allow hESCs to progressively and uniformly differentiate into the chondrogenic lineage. As described above, undifferentiated pluripotent hESCs subjected to micromass culture in the presence of BMP2 (or BMP2 and TGFβ together) directly undergo progressive and quite uniform differentiation into the chondrogenic lineage without prior EB formation.

The direct and progressive chondrogenic differentiation that pluripotent undifferentiated hESCs undergo has enabled the characterization of progenitor cells in different phases of the chondrogenic lineage which can be tested and compared for their abilities to repair damaged or diseased human cartilage using cell based tissue engineering therapies. By gene expression profiling of BMP2-treated hESC micromass cultures harvested at different periods of culture, cells that are just entering into the chondrogenic lineage (day 3 cultures i.e., chondroprogenitors), cells which are in an early phase of overt chondrocyte differentiation (day 4 cultures i.e., early chondrocytes), and cells which have uniformly undergone overt differentiation into chondrocytes, but have not undergone hypertrophic maturation (day 7 and 14 cultures i.e., fully differentiated chondrocytes) were identified.

In particular, day 3 hESC micromass cultures are characterized by upregulated expression of the transcriptional regulators Sox9 and Brachyury, but do not exhibit upregulated expression of aggrecan, a definitive highly specific molecular marker of overtly differentiated chondrocytes, and exhibit little or no Alcian blue positive matrix. Thus, day 3 cultures have entered into the chondrogenic lineage, but have not yet undergone overt differentiation into chondrocytes. This characteristic of progenitor cells at such an early stage in the chondrogenic lineage is useful in repairing cartilage defects. Cells in a very early phase of the chondrogenic lineage are more responsive to signals that promote their participation in repair compared to cells at late stages of the lineage.

Cell populations at certain stages of development are preferred for certain clinical indications. For example, day 2-4 cells (chondrogenic progenitors or early chondrocytes) integrate better into damaged tissue and cartilage and elicit better and longer lasting repair.

Chondroprogenitors (day 2-3 cells) are preferentially used for limb or finger regeneration, mensical or ligament repair, and fracture repair. Early chondrocytes (day 4 cells) are used for repair of articular cartilage defects due to injury, for repair or prevention of articular cartilage damage due to chronic disease (OA or RA), for regeneration and replacement of lost cartilage tissue due to trauma or congenital defect, for meniscal repair, and for repair of fibrocartilage of the temporomandibular joint. More fully differentiated chondrocytes are suitable for indications such as for articular cartilage repair following acute or traumatic injury, or for repair or prevention of articular cartilage due to disease (OA or RA), as well as for fracture repair via endochondral ossification. Each stage is useful for modeling of cartilage development and differentiation, and iPSC derived cells in particular are useful for patient specific repair and regeneration, as well as for modeling of human disease, design and testing of targeted therapeutics, and for disease-specific repair of genetically compromised cartilage tissue.

Day 4 BMP2-treated hESC micromass cultures exhibit further upregulation in the expression of Sox9 and Brachyury, and exhibit a greater than 4-fold upregulation in the expression of the definitive cartilage marker aggrecan, indicating that the day 4 cultures are in an early phase of overt differentiation into chondrocytes. Day 7 and 14 cultures are characterized by a downregulation in expression of Sox9 and Brachyury accompanied by an about 8-fold upregulation in the expression of the cartilage markers aggrecan and Col2a1. A uniform Alcian blue positive matrix is also present throughout the extent of the day 7 and 14 cultures and type II collagen detectable by immunostaining is present throughout the extent of the cultures. Day 7 and 14 cultures do not express markers of hypertrophic chondrocyte maturation such as Col10a1, Ihh, or osteopontin. Thus, day 7 and 14 cultures have undergone overt differentiation into chondrocytes, but have not undergone hypertrophic maturation. This is significant in considering utilization of the cells for articular cartilage repair, as the chondrocytes comprising articular cartilage do not normally undergo hypertrophic maturation, and indeed inappropriate hypertrophic maturation of articular chondrocytes is characteristic of osteoarthritis. The fact that the chondrocytes of day 7 and/or 14 cultures have not undergone hypertrophic maturation makes these cells attractive candidates for repair of cartilage defects.

Micromass Cultures of hESCs for Identification of Factors Involved in the Determination Process that Channels Progenitor Cells into the Chondrogenic Lineage Although some of the regulatory genes such as Sox9 that control the onset of cartilage differentiation have been identified, little is known about the genes and other factors that are involved in the progressive determination or commitment of embryonic progenitor cells into the chondrogenic lineage. The progressive differentiation of hESCs in micromass culture in the presence of BMP2 provides suitable system for defining factors involved in these early determinative events. Analysis of the transcriptomes of cells in various stages of their lineage progression from an undifferentiated pluripotent hESC into a chondrocyte facilitates the identification of genes, signaling molecules, and regulatory networks that control early chondrogenic lineage commitment events, and enable delineation of unknown genes involved in the determination process.

The gene expression profiling described above indicates a role for the transcription factor Brachyury in channeling cells into the chondrogenic lineage. Previous studies have shown that Brachyury, which is a T-box transcription factor, is highly expressed during gastrulation, and plays an essential role in primary mesoderm formation (Herrmann B G, 1995 Seminars in Developmental Biology, 6:385-394). Later in development, Brachyury is expressed in the lateral mesoderm at the onset of limb bud formation and subsequently by the prechondrogenic mesenchymal cells that will give rise to cartilage in the developing limb (Liu C et al., 2003 Development, 130:1327-1337). As described above, expression of Brachyury is upregulated (24-fold) as hESC micromass cultures treated with BMP2 are just entering into the chondrogenic lineage as assayed by upregulated expression of the chondrogenic transcription factor Sox9. The concomitant upregulation of Brachyury and Sox9 expression occurs before upregulation of the expression of the definitive cartilage marker aggrecan. The expression of Brachyury and Sox9 then concomitantly increase even further as the BMP2-treated hESC micromass cultures initiate upregulated expression of aggrecan. After the onset of chondrogenesis, the expression of Brachyury and Sox9 concomitantly decrease to negligible levels as overt cartilage differentiation occurs. This expression pattern during the progressive differentiation of BMP2-treated undifferentiated pluripotent hESCs into chondrocytes indicates that Brachyury is involved in regulating the early commitment of mesodermal progenitor cells into the chondrogenic lineage.

It has been demonstrated that Brachyury expression is upregulated at the onset of the chondrogenic differentiation of the mesenchymal cell line C3H10T1/2 in response to BMP2 signaling (Hoffmann A et al., 2002 J Cell Sci, 115:769-781), and forced expression of Brachyury promotes the expression of Sox9 and the chondrogenic differentiation of C3H10T1/2 cells (Hoffmann A et al., 2002 J Cell Sci, 115:769-781). Moreover, a dominant negative form of Brachyury impairs BMP2-stimulated chondrogenic differentiation of C3H10T1/2 cells (Hoffmann A et al., 2002 J Cell Sci, 115: 769-781). It has been suggested that Brachyury may endow prechondrogenic progenitor cells such as C3H101/2 cells with the ability to undergo chondrogenic differentiation in response to BMP2 (Hoffmann A et al., 2002 J Cell Sci, 115:769-781). The results described above indicate that Brachyury expression is upregulated as hESCs enter into the chondrogenic lineage in response to BMP2 is consistent with previous studies. These studies indicate that Brachyury is involved in the determination process that channels progenitor cells into the chondrogenic lineage.

EXAMPLE 5

Differentiation of Human Embryonic Stem Cells into the Chondrogenic Lineage

Figure 9:
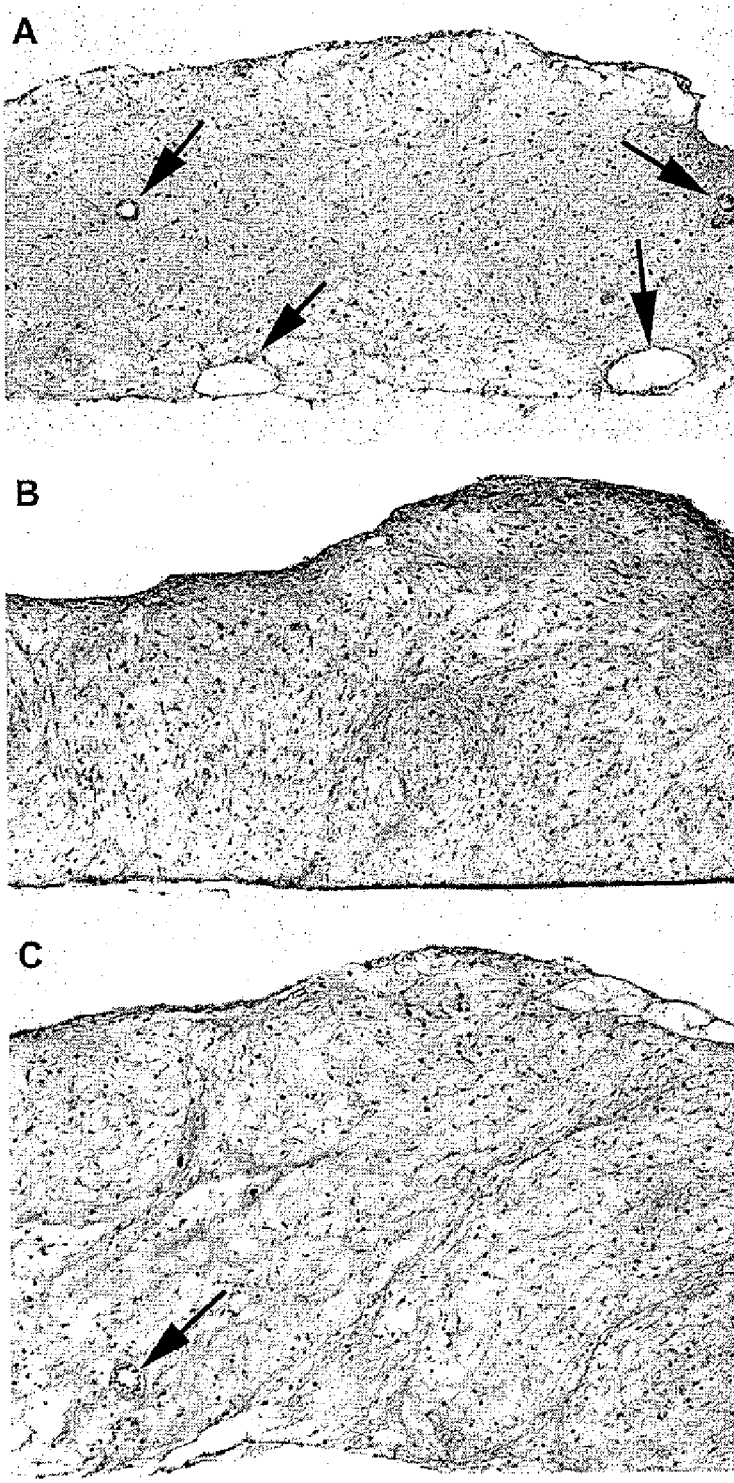
FIGS. 9A-C are photomicrographs with a Table (Table 1) below FIG. 9C.

As shown in FIG. 4C, extracellular cartilage-characteristic type II collagen is present throughout BMP2-treated hESC micromass cultures as detected by immunostaining of sagittal sections of the cultures with a type II collagen antibody. In addition, cells whose cytoplasm stains with a monoclonal antibody against the globular domain of the cartilage marker aggrecan are present throughout BMP-2-treated hESC micromass cultures (FIG. 9), indicating that virtually all of the cells that are surrounded by a type II collagen extracellular matrix are expressing the cartilage marker aggrecan as assayed by immunostaining with a cell autonomous marker.

Figure 4:
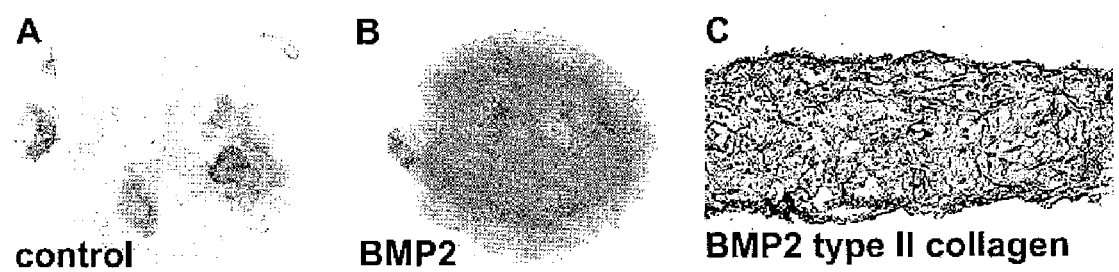
FIGS. 4A-C are photomicrographs showing the effect of BMP2 on accumulation of Alcian blue cartilage matrix and type II collagen in micromass cultures established directly from undifferentiated pluripotent hESCs: (A) Alcian blue stained day 14 untreated control culture; (B) Alcian blue stained day 14 BMP2-treated culture; and (C) a sagittal section through a day 14 BMP2-treated culture immunostained with a type II collagen antibody.
Figure 5:
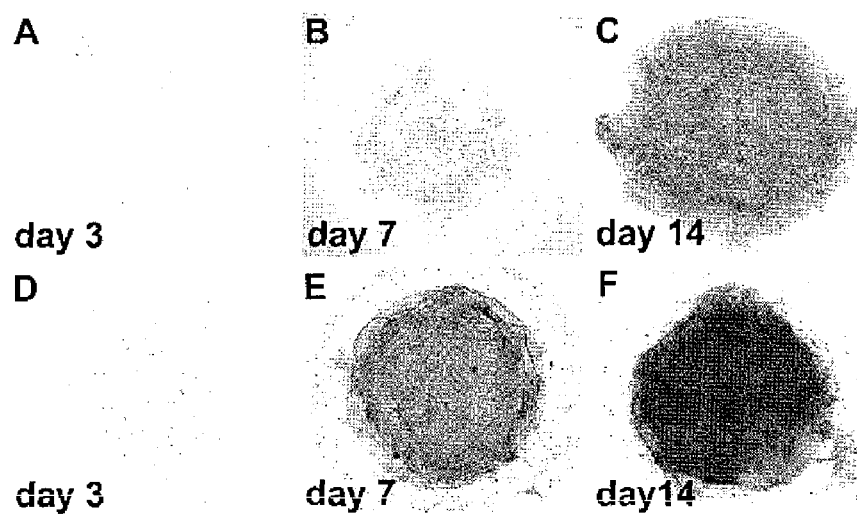
FIGS. 5A-F are photomicrographs showing a time course of Alcian blue matrix accumulation in BMP2-treated micromass cultures established from undifferentiated pluripotent hESCs: (A-C) cultures were supplemented with BMP2 in "chondrogenic medium" on day 2; (D-F) cultures were provided with "chondrogenic medium" lacking BMP2 on day 2, and then supplemented with BMP2 on day 3.
Figure 6:
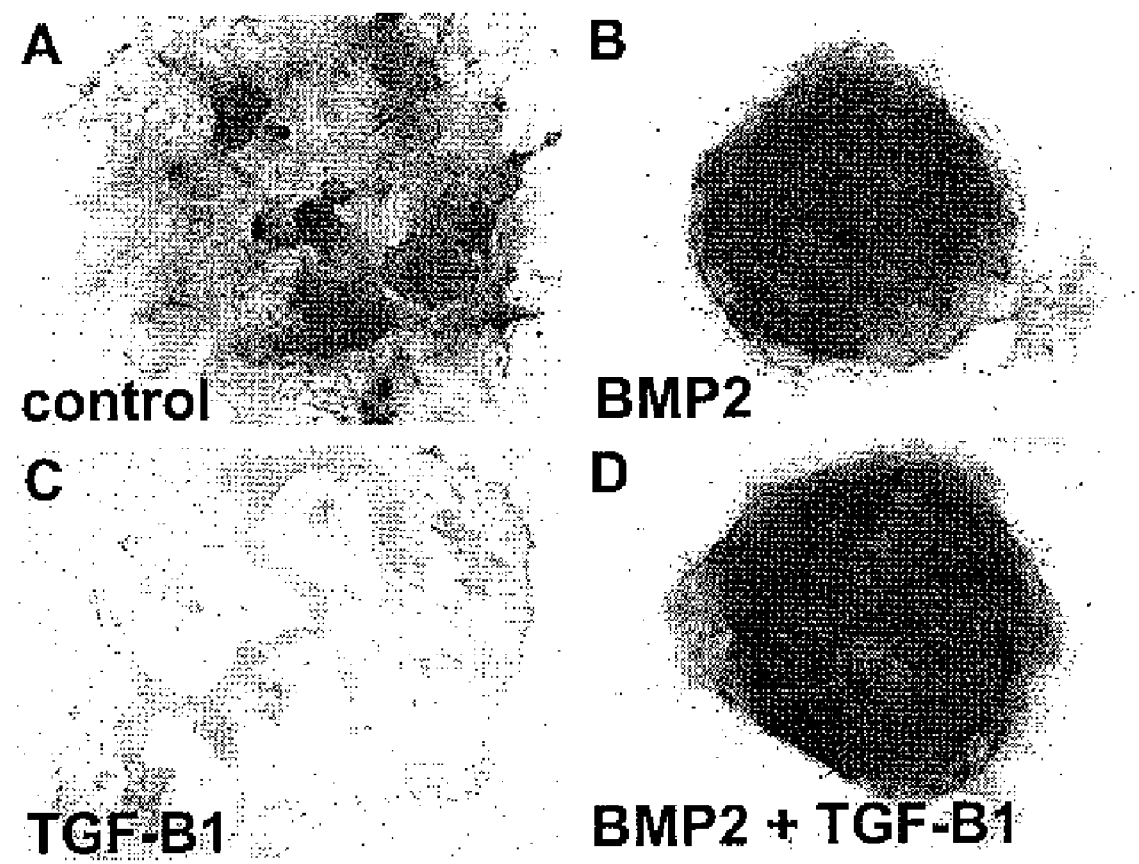
FIGS. 6a-D are photomicrographs showing Alcian blue stained day 14 micromass cultures established from undifferentiated pluripotent hESCs: (A) untreated control culture; (B) BMP2-treated culture; (C) TGFβ1-treated culture; (D) culture treated with both BMP2 and TGFβ1.
Figure 10:
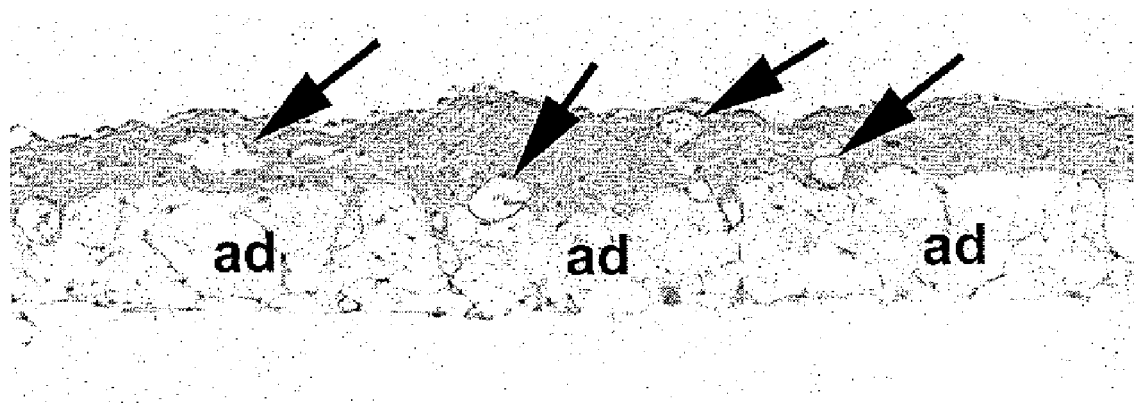
FIG. 10 is a photomicrograph showing an Alcian blue and Nuclear Fast Red stained sagittal section through a BMP2+TGF-β1-treated micromass culture established from embryoid body (EB) cells. In addition to Alcian blue-stained chondrogenic tissue, a large amount of adipose tissue (ad) is present, as well tubules (arrows).

The accumulation of cartilage matrix in cultures is routinely monitored by whole mount staining of the intact cultures with Alcian blue, pH 1.0, which stains the sulfated proteoglycans of the matrix. Quite uniform accumulation of Alcian blue stainable matrix is detectable by whole mount staining in hESC micromass cultures treated with either BMP2 alone or BMP2 plus TGF-131 (FIGS. 4-6). To histologically evaluate the extent of cartilage differentiation, sagittal sections of hESC micromass cultures were stained with Alcian blue and counterstained with the nuclear stain Nuclear Fast Red. Cells surrounded by an Alcian blue stainable extracellular matrix are present throughout virtually the entire extent of histological sections through hESC micromass cultures treated with either BMP2 alone (FIG. 10A) or with BMP2 plus TGF-$\beta$1 (FIGS. 10B and 10C). In addition to the extensive cartilage tissue, the BMP2-treated hESC cultures contained a small number of tubular structures (FIG. 10A; arrows). The number of tubules that are detectable is considerably reduced when the cultures are supplied with TGF-131 as well as BMP2, and the tubules constitute only a very small percentage of the cultures. Thus, although not completely homogeneous, chondrogenic differentiation in hESC micromass cultures treated with both BMP2 and TGF-$\beta$1 occurs quite uniformly and is considerably more robust and extensive than in other cultures systems that have been previously reported. Indeed, BMP2 TGF-$\beta$-treated micromass cultures established from embryoid body (EB) cells are quite heterogeneous consisting not only of chondrogenic tissue, but also a large amount of adipose tissue, as well tubules (FIG. 11).

Figure 12:
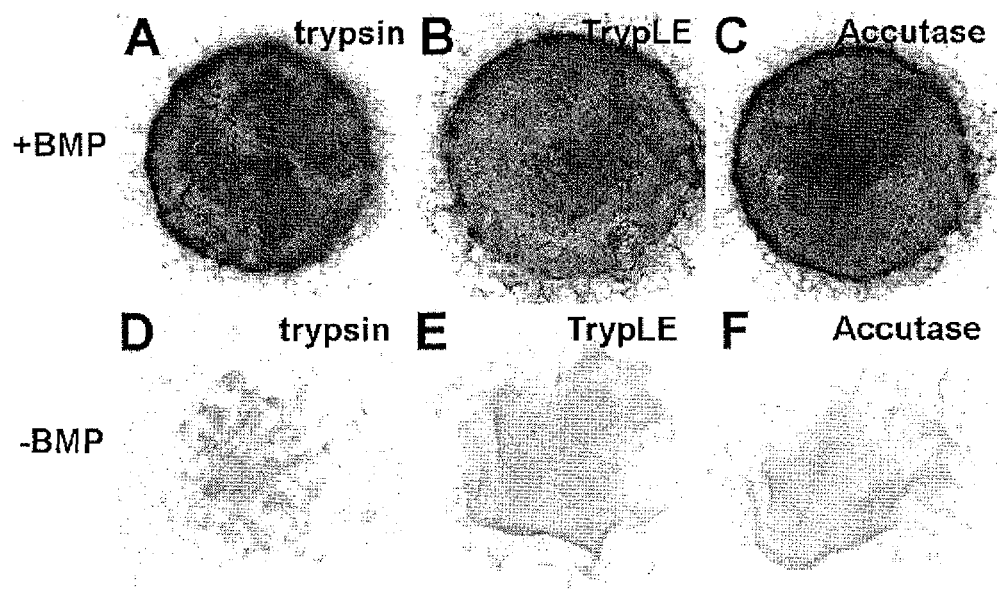
FIG. 12 (A-C) shows micromass cultures of BMP2-supplemented iPSC previously dissociated with trypsin (A), TrypLE Select (B) or Accutase (C) and stained whole-mount with Alcian blue after 7 days of culture. Comparable accumulation of Alcian blue is evident in each culture.
Figure 13:
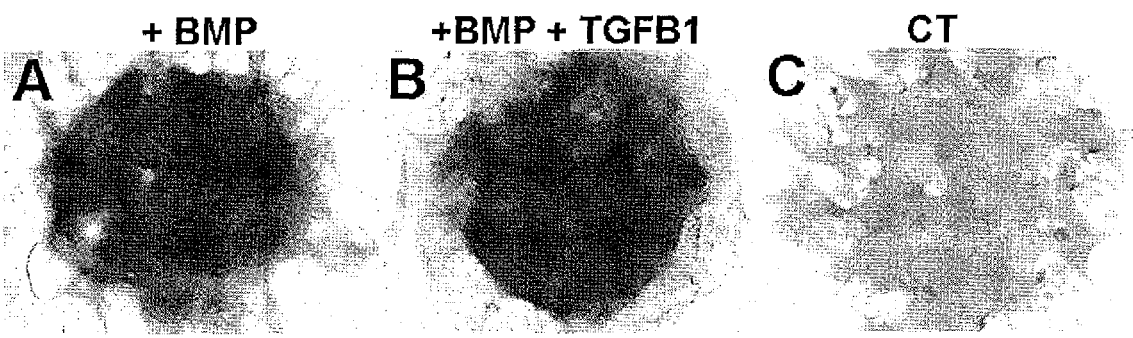
FIGS. 13A-C are photomicrographs demonstrating chondrogenic differentiation of iPSC micromass cultures in response to combined BMP2 and TGFB1.
Figure 14:
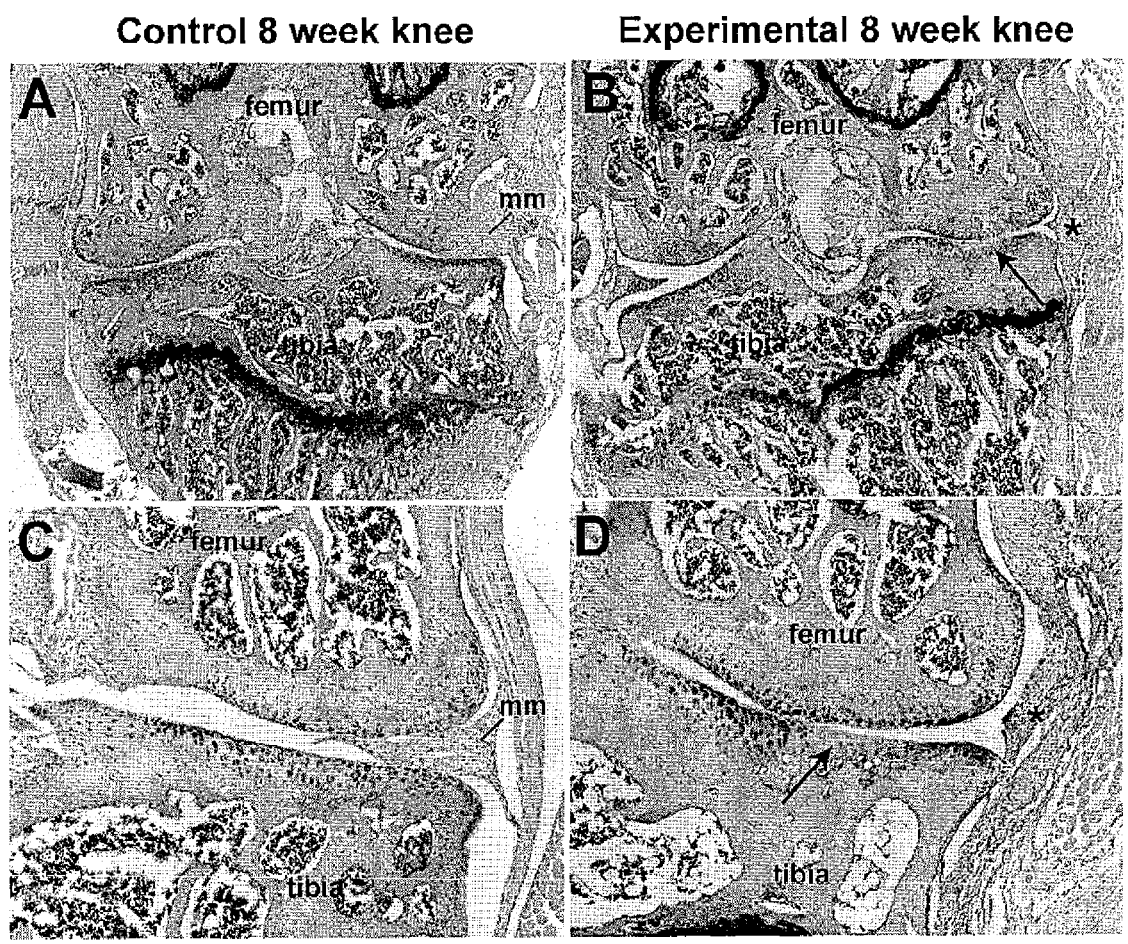
FIGS. 14 C and D are higher magnification views of A and B.
Figure 15:
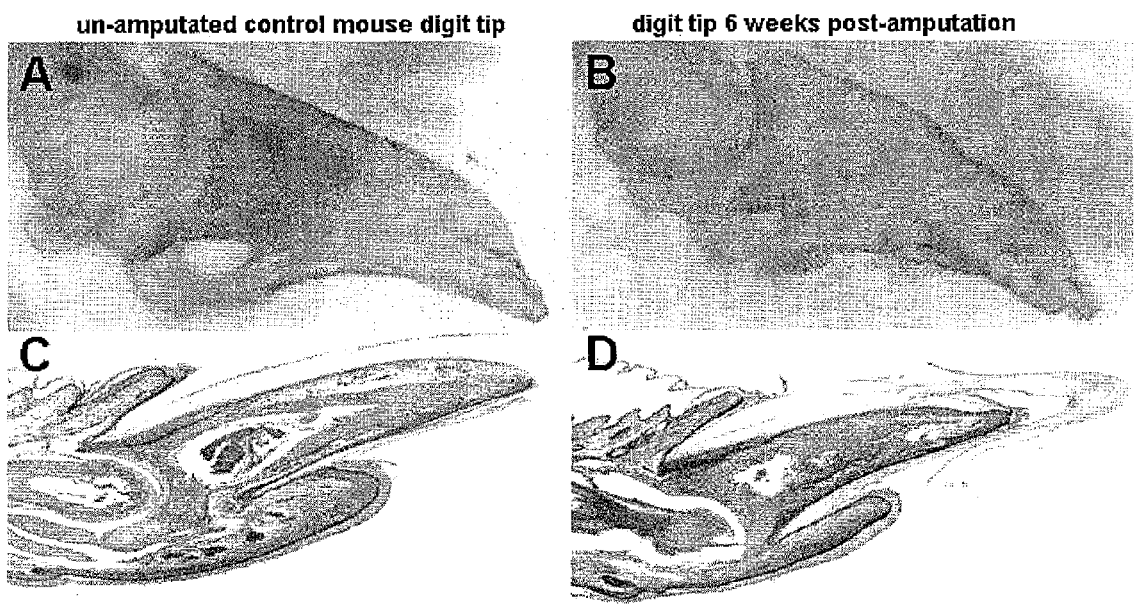
FIGS. 15A-D are photomicrographs demonstrating the mouse digit tip regeneration model.

EXAMPLE 6 iPSC-Derived Chondrocytes for Regenerative Medicine and Human Disease Modeling iPSCs are obtained from a patients own cells, thereby offering a means for patient specific cell mediated therapy and regenerative medicine (Amabile G and Meissner A 2009 Trends Mol Med 15:59-68). As shown in FIGS. 11, 12, and 13, iPSC undergo directed and progressive differentiation into the chondrogenic lineage by the methods described herein.

Figure 11:
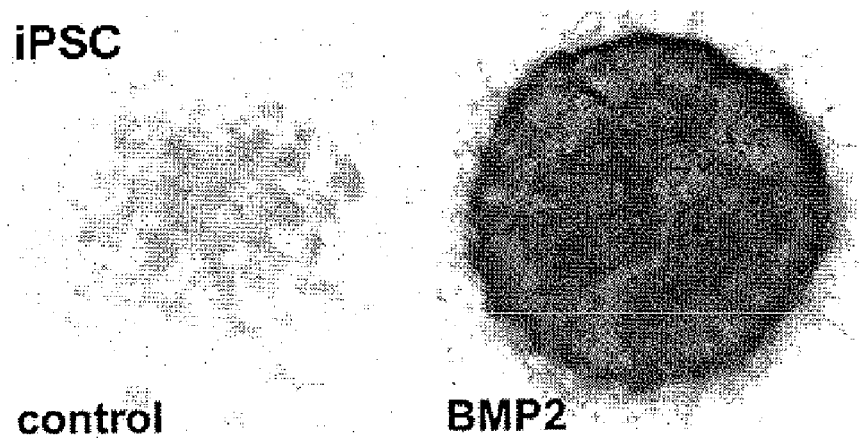
FIG. 11 is a photomicrograph demonstrating chondrogenic differentiation as assayed by Alcian blue staining of cartilage matrix of an iPS cell line derived from human foreskin fibroblasts subjected to the methods described herein.

FIG. 11 (A) shows a control micromass culture of iPSC maintained without BMP2 supplementation for 14 days, which exhibits little Alcian blue-positive matrix accumulation. FIG. 11 (B) shows a day 14 BMP2 treated iPSC micromass culture, which shows intense and widespread Alcian blue staining present throughout the extent of the culture.

To verify the progression of chondrogenic differentiation by the BMP2-supplemented iPSC-derived micromass cultures, quantitative real-time RT-PCR of the mRNA expression of marker genes characteristic of the chondrogenic lineage including Brachyury, sox9, Col2a1 and aggrecan was used. Levels of these marker genes underwent similar upregulation during the culture period as do hESC micromass cultures supplemented with BMP2. In addition, expression of Osteopontin mRNA, a marker of hypertrophic chondrocytes, was negligible in BMP2-supplemented iPSC micromass cultures. Thus, micromass cultures of iPSC using the present methods undergo progressive differentiation into the chondrogenic lineage and also do not undergo hypertrophy in vitro.

Studies were carried out to compare chondrogenic differentiation by micromass cultures established from iPSC dissociated to single cells by three different enzymatic approaches: trypsin-EDTA, Accutase or TrypLE Select. As shown in FIG. 12, after 7 days, BMP2-supplemented micromass cultures established from iPSC previously dissociated with either trypsin-EDTA (FIG. 12A), TrypLE Select (FIG. 12B) or Accutase (FIG. 12C) each exhibit comparable accumulation of intensely stained and widespread Alcian blue-positive matrix, indicating that each dissociation method is equally effective in producing single iPSC that can successfully undergo chondrogenic differentiation in the protocol in response to BMP2. Little Alcian blue positive matrix is present in cultures maintained without BMP2 supplementation (FIGS. 12D-F).

As shown in FIG. 13, iPSC micromass cultures undergo comparable chondrogenic differentiation as assayed by widespread and intense Alcian Blue staining after 14 days of culture in response to BMP2 (FIG. 13A) as well as a combination of BMP2 and TGFβ1 (FIG. 13B), in contrast to iPSC micromass cultures which received no BMP2 supplementation which accumulate little Alcian blue-positive matrix (FIG. 13C).

Thus, the method is useful for generation of iPSC for patient specific cartilage repair and restoration therapies including articular cartilage defect repair of joints due to injury or chronic disease such as OA or RA; and for limb regeneration, meniscal or ligament defect repair, and fracture repair, using approaches described above.

iPSC obtained from individuals with genetic disorders provide a means for disease modeling and screening for the design and testing of targeted therapeutics (Laustriat D et al., 2010 Biochem Soc Trans 38:1051-1057; Lengner CJ 2010 Ann NY Acad Sci 1192: 38-44). iPSC when combined with gene targeting provide an approach for monogenic disease treatment (Wong GKY and Chiu AT 2010 Biotechnol Adv 28:715-724).

Figure 16:
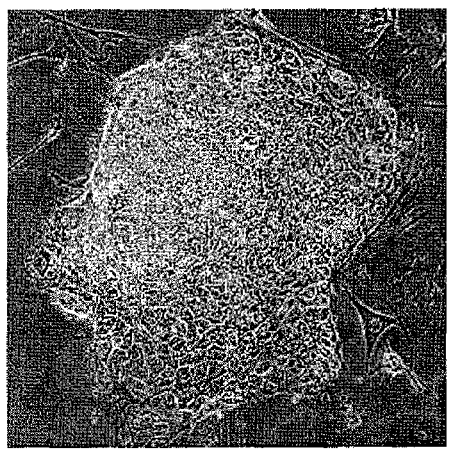
FIGS. 16A-B are photomicrographs demonstrating derivation of iPSCs from human fibroblasts from a patient with a genetic cartilage disorder (chondrodysplasia).
Figure 16:
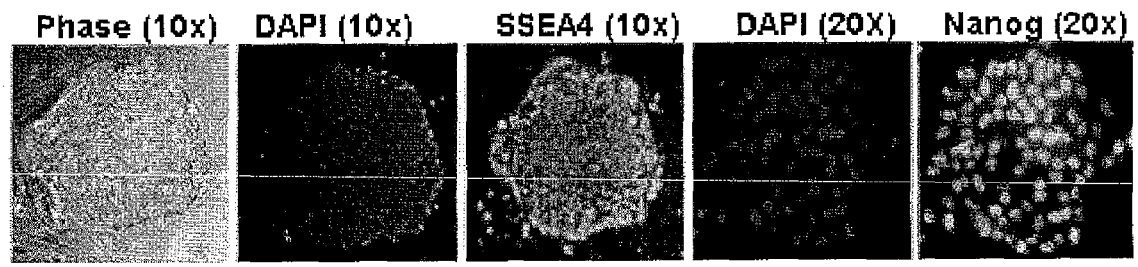

As shown in FIG. 16, iPSC were generated from a human patient with chondrodysplasia. iPSC from human patients with genetic cartilage disorders are induced to differentiate into chondrogenic lineage using the methods described herein. The high density culture methods, including the high density micromass approach which was used to induce chondrogenic differentiation of hESC and iPSC is suitable for use as a toxicology test (Piersma AH 2004 Toxicol Lett 149:147-153; Ponce RA 2001 Curr Protoc Toxicol 13: 13.3); as a genomic screen to identify novel genetic regulators of cartilage development (James C G et at., 2005 Mol Biol Cell 16:5316-5333), for detection of developmental toxins affecting chondrogenesis (Hanse et al 2001 Free Radic Biol Med 31: 1582-1592) and for mechanistic evaluation of potential skeletal dysplasia therapeutics (Woods A et al., 2007 Endocrinol 148: 5030-5041). iPSC-derived from patients with genetic disorders of cartilage (e.g., chondrodysplasia or achondroplasia) and induced to undergo chondrogenic differentiation by the methods described herein are useful for modeling of the disease process and design and testing of drug therapies. Gene profiling of the iPSC-derived chondrodysplastic chondrogenic cells is used to identify key genes and factors which mediate the disease process, which provides disease-specific targets for therapeutic intervention. Targeted therapeutics for the disease are tested in vitro by determining the response of the diseased iPSC-derived chondrogenic cells produced by the method to the agents in vitro. iPSC-derived disease-specific chondrogenic cells produced by the method are also used in conjunction with gene therapy as an approach to restore normal cartilage structure or function in the genetically-diseased patients.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for direct differentiation of human embryonic stem cells (hESCs) into chondrogenic cells comprising:
   providing a population of hESCs on a substrate, said population being substantially free of embryoid bodies (EBs);
   detaching said hESCs from said substrate and dissociating said hESCs;
   establishing a high-density micromass culture of said hESCs;
   contacting said population with a bone morphogenetic protein (BMP) no sooner than 24 hours after establishing the high-density micromass culture;
   wherein said hESCs directly differentiate without EB formation into a population comprising at least 85% chondrogenic cells.

2. The method of claim 1, wherein said substrate is a feeder layer comprising mouse embryonic fibroblasts (MEF).

3. The method of claim 1, wherein said substrate is a polymeric or gelatinous substrate or scaffold.

4. The method of claim 1, further comprising administering contacting said hESCs with transforming growth factor beta no sooner than 24 hours after establishing the high-density micromass culture.

5. The method of claim 1, wherein said BMP comprises BMP-2 and wherein said BMP-2 is administered about 48 hours after establishing said high-density micromass culture.

6. The method of claim 1, wherein said hESCs differentiate into fully differentiated chondrocytes within about 14 days.

7. The method of claim 1, wherein said hESCs differentiate into fully differentiated chondrocytes within about 7 days.

8. The method of claim 1, wherein said hESCs differentiate into chondroprogenitor cells within about 2-3 days.

9. The method of claim 1, wherein said hESCs differentiate into early chondrocytes within about 4 days.

10. The method of claim 1, wherein the population comprises at least about 95% chondrogenic cells.

11. The method of claim 1, wherein said hESCs are dissociated with trypsin, TrypLE Select™, or Accutase™.

12. The method of claim 1, further comprising contacting said hESCs with Rho-associated kinase (ROCK) inhibitor.

13. A method for direct differentiation of induced pluripotent stem cells (iPSCs) into chondrogenic cells comprising:
providing a population of iPSCs on a substrate, said population being substantially free of EBs;
detaching said iPSCs from said substrate and dissociating said iPSCs;
establishing a high-density culture of said iPSCs;
contacting said iPSCs with a bone morphogenetic protein (BMP) no sooner than 24 hours after establishing the high-density micromass culture;
wherein said iPSCs directly differentiate without EB formation into a population comprising at least 85% chondrogenic cells.

14. The method of claim 13, wherein said substrate is a feeder layer comprising mouse embryonic fibroblasts (MEF).

15. The method of claim 13, wherein said substrate is a polymeric or gelatinous substrate or scaffold.

16. The method of claim 13, further comprising contacting said iPSCs with transforming growth factor beta no sooner than 24 hours after establishing the high-density micromass culture.

17. The method of claim 13, wherein said BMP is BMP-2.

18. The method of claim 17, wherein said BMP-2 is administered 48 hours after initiation of said iPSC high-density micromass culture.

19. The method of claim 13, wherein said iPSCs differentiate into full differentiated chondrocytes within about 14 days.

20. The method of claim 13, wherein said iPSCs differentiate into fully differentiated chondrocytes within 7 days.

21. The method of claim 13, wherein said iPSCs differentiate into chondroprogenitor cells within about 2-3 days.

22. The method of claim 13, wherein said iPSCs differentiate into early chondrocytes within about 4 days.

23. The method of claim 13, wherein at least about 95% of said iPSCs differentiate into cells of the chondrogenic lineage.

24. The method of claim 13, wherein said iPSCs are dissociated with trypsin, TrypLE Select™, or Accutase™.

25. The method of claim 13, further comprising contacting said iPSCs with Rho-associated kinase (ROCK) inhibitor.

26. The method of claim 1, wherein the BMP is BMP-2, and wherein the BMP-2 is added at a concentration of between 25 ng/ml to 200 ng/ml.

27. The method of claim 26, further comprising administering contacting said hESCs with transforming growth factor beta (TGF-β) no sooner than 24 hours after establishing the high-density micromass culture.

28. The method of claim 27, wherein the ratio of BMP-2 to TGF-β is between 5:1 to 20:1.

* * * * *